United States Patent
Relton et al.

(10) Patent No.: US 10,119,979 B2
(45) Date of Patent: Nov. 6, 2018

(54) METHODS OF TREATING STROKE AND TRAUMATIC BRAIN INJURY USING HUMANIZED AQC2 ANTI-VLA-1 ANTIBODIES

(75) Inventors: Jane K. Relton, Belmont, MA (US); Humphrey Gardner, Salem, MA (US)

(73) Assignee: Biogen MA Inc., Cambridge, MA (US)

( * ) Notice: Subject to any disclaimer, the term of this patent is extended or adjusted under 35 U.S.C. 154(b) by 38 days.

(21) Appl. No.: 12/301,988

(22) PCT Filed: May 24, 2007

(86) PCT No.: PCT/US2007/069654
§ 371 (c)(1),
(2), (4) Date: Nov. 21, 2008

(87) PCT Pub. No.: WO2007/140249
PCT Pub. Date: Dec. 6, 2007

(65) Prior Publication Data
US 2010/0233159 A1    Sep. 16, 2010

Related U.S. Application Data

(60) Provisional application No. 60/809,149, filed on May 25, 2006.

(51) Int. Cl.
| | | |
|---|---|---|
| G01N 33/53 | (2006.01) | |
| A61K 38/00 | (2006.01) | |
| A61K 39/00 | (2006.01) | |
| A61K 39/395 | (2006.01) | |
| C07K 16/00 | (2006.01) | |
| C12P 21/08 | (2006.01) | |
| A61K 49/16 | (2006.01) | |
| G01N 33/68 | (2006.01) | |
| A61K 31/00 | (2006.01) | |
| A61K 38/19 | (2006.01) | |
| A61K 38/49 | (2006.01) | |
| C07K 16/28 | (2006.01) | |

(52) U.S. Cl.
CPC ......... *G01N 33/6896* (2013.01); *A61K 31/00* (2013.01); *A61K 38/193* (2013.01); *A61K 38/49* (2013.01); *C07K 16/2842* (2013.01); *A61K 2039/505* (2013.01); *G01N 2800/2871* (2013.01)

(58) Field of Classification Search
CPC .......... A61K 2300/00; A61K 2039/505; A61K 38/49; A61K 9/0019; A61K 39/00; A61K 38/55; A61K 39/395; A61K 38/1709; A61K 49/0056; A61K 38/484; A61K 47/48415; C07K 2317/76; C07K 2316/96; C07K 2317/565; C07K 2317/21; C07K 2317/92; C07K 2317/55; C07K 2319/00; C07K 2317/30; C07K 2317/52; C07K 2317/24; C07K 14/705; C07K 14/78; C07K 16/18; C07K 2318/10; C07K 16/2842; C07K 2317/56; G01N 2800/2871; G01N 33/6896; A61L 27/54
See application file for complete search history.

(56) References Cited

U.S. PATENT DOCUMENTS

| | | |
|---|---|---|
| 4,683,195 A | 7/1987 | Mullis et al. |
| 5,391,481 A | 2/1995 | Chess et al. |
| 5,530,101 A | 6/1996 | Queen et al. |
| 5,565,332 A | 10/1996 | Hoogenboom et al. |
| 5,585,089 A | 12/1996 | Queen et al. |
| 5,648,260 A | 7/1997 | Winter et al. |
| 5,693,761 A | 12/1997 | Queen et al. |
| 5,693,762 A | 12/1997 | Queen et al. |
| 5,733,743 A | 3/1998 | Johnson et al. |
| 5,773,743 A | 6/1998 | Ogawa et al. |
| 5,788,966 A | 8/1998 | Chess et al. |
| 5,789,650 A | 8/1998 | Lonberg et al. |
| 5,798,230 A | 8/1998 | Bornkamm et al. |
| 5,827,690 A | 10/1998 | Meade et al. |
| 5,849,992 A | 12/1998 | Meade et al. |
| 5,855,888 A | 1/1999 | Nishida et al. |
| 5,859,205 A | 1/1999 | Adair et al. |
| 6,001,961 A | 12/1999 | Jonczyk et al. |
| 6,016,159 A | 1/2000 | Faris |
| 6,075,181 A | 6/2000 | Kucherlapati et al. |
| 6,127,524 A | 10/2000 | Casipit et al. |
| 6,150,584 A | 11/2000 | Kucherlapati et al. |
| 6,162,963 A | 12/2000 | Kucherlapati et al. |
| 6,180,370 B1 | 1/2001 | Queen et al. |
| 6,291,650 B1 | 9/2001 | Winter et al. |
| 6,300,064 B1 | 10/2001 | Knappik et al. |
| 6,303,313 B1 | 10/2001 | Wigler et al. |
| 6,307,026 B1 | 10/2001 | King et al. |
| 6,326,403 B1 | 12/2001 | Holzemann et al. |

(Continued)

FOREIGN PATENT DOCUMENTS

| | | |
|---|---|---|
| EP | 239400 A2 | 9/1987 |
| EP | 0843691 A1 | 5/1998 |

(Continued)

OTHER PUBLICATIONS

Becker et al. Stroke 2001; 32:206-211.*
Boerner et al. (1991) J. Immunol. 147:86-95.
Schiro (1991) Cell 67:403-410.

(Continued)

*Primary Examiner* — Chang-Yu Wang
(74) *Attorney, Agent, or Firm* — McCarter & English, LLP; Jonathan M. Sparks; Marcie B. Clarke

(57) ABSTRACT

Methods and compositions for treating stroke are disclosed.

19 Claims, 2 Drawing Sheets
Specification includes a Sequence Listing.

(56) References Cited

U.S. PATENT DOCUMENTS

| | | | |
|---|---|---|---|
| 6,407,213 B1 | 6/2002 | Carter et al. | |
| 6,497,878 B1 | 12/2002 | Yamashita et al. | |
| 6,602,503 B1 | 8/2003 | Lobb et al. | |
| 6,632,927 B2 | 10/2003 | Adair et al. | |
| 6,652,856 B2 | 11/2003 | Gotwals et al. | |
| 6,955,810 B2 | 10/2005 | De Fougerolles | |
| 7,358,054 B2* | 4/2008 | Lyne et al. | 435/7.1 |
| 7,462,353 B2 | 12/2008 | De Fougerolles | |
| 7,612,181 B2* | 11/2009 | Wu et al. | 530/387.3 |
| 7,723,073 B2* | 5/2010 | Karpusas et al. | 435/69.1 |
| 7,745,396 B2* | 6/2010 | Lucas | 514/16.4 |
| 7,910,099 B2 | 3/2011 | Karpusas | |
| 8,084,028 B2 | 12/2011 | Karpusas | |
| 8,084,029 B2 | 12/2011 | Hansen et al. | |
| 8,084,031 B2 | 12/2011 | Gotwals | |
| 8,557,240 B2 | 10/2013 | Gotwals et al. | |
| 2002/0197233 A1* | 12/2002 | Relton | A61K 38/2264 424/85.1 |
| 2003/0070185 A1 | 4/2003 | Jakobovits et al. | |
| 2003/0232333 A1 | 12/2003 | Ladner et al. | |
| 2004/0081651 A1* | 4/2004 | Karpusas et al. | 424/146.1 |
| 2004/0208870 A1 | 10/2004 | Allan | |
| 2005/0226877 A1 | 10/2005 | Gotwals et al. | |
| 2006/0115473 A1* | 6/2006 | Relton | C07K 16/2842 424/133.1 |
| 2006/0286112 A1* | 12/2006 | Kellermann et al. | 424/155.1 |
| 2007/0071675 A1* | 3/2007 | Wu et al. | 424/1.49 |
| 2008/0118496 A1 | 5/2008 | Medich et al. | |
| 2009/0238762 A1 | 9/2009 | Totoritis et al. | |
| 2010/0027216 A1 | 2/2010 | Matsushima et al. | |
| 2010/0233159 A1 | 9/2010 | Relton et al. | |
| 2012/0087925 A1 | 4/2012 | Gotwals et al. | |
| 2012/0177638 A1 | 7/2012 | Karpusas et al. | |
| 2014/0017261 A1 | 1/2014 | Totoritis | |
| 2014/0110827 A1 | 4/2014 | Tsukahara et al. | |
| 2014/0127195 A1* | 5/2014 | Relton | C07K 16/2842 424/133.1 |
| 2014/0154259 A1 | 6/2014 | De Fougerolles et al. | |
| 2016/0152709 A1* | 6/2016 | Ticho | C07K 16/2842 424/133.1 |

FOREIGN PATENT DOCUMENTS

| | | | |
|---|---|---|---|
| EP | 843961 A1 | 5/1998 | |
| JP | 08131185 A | 5/1996 | |
| JP | 2005-507639 A | 3/2005 | |
| WO | 9007861 A1 | 7/1990 | |
| WO | 9313798 A1 | 7/1993 | |
| WO | 199417828 A2 | 8/1994 | |
| WO | 9519790 A1 | 7/1995 | |
| WO | 9634096 A1 | 10/1996 | |
| WO | 9711718 A1 | 4/1997 | |
| WO | 9718838 A1 | 5/1997 | |
| WO | 1998/06417 A1 | 2/1998 | |
| WO | 9856418 A1 | 12/1998 | |
| WO | 99/61040 A2 | 12/1999 | |
| WO | 00/20459 A1 | 4/2000 | |
| WO | 00/72881 A1 | 12/2000 | |
| WO | 2000/72881 A1 | 12/2000 | |
| WO | 0078221 A1 | 12/2000 | |
| WO | 0173444 A2 | 10/2001 | |
| WO | 0196365 A1 | 12/2001 | |
| WO | 02072030 A2 | 9/2002 | |
| WO | 2002/083854 A2 | 10/2002 | |
| WO | 02083854 A2 | 10/2002 | |
| WO | 2002083854 | 10/2002 | |
| WO | 2003068262 | 8/2003 | |
| WO | 2005/016883 A2 | 2/2005 | |
| WO | 2005/019200 A2 | 3/2005 | |
| WO | 2005019200 | 3/2005 | |
| WO | WO2005/019177 | * 3/2005 | C07D 211/58 |
| WO | 2006/034035 A2 | 3/2006 | |
| WO | 2006124269 | 11/2006 | |
| WO | 2006133286 A2 | 12/2006 | |
| WO | 2007124090 A2 | 11/2007 | |
| WO | 2007/140249 A1 | 12/2007 | |
| WO | 2010102241 A1 | 9/2010 | |
| WO | 2011084750 A1 | 7/2011 | |
| WO | 2012106497 A2 | 8/2012 | |

OTHER PUBLICATIONS

Co et al. (1991) Proc. Natl. Acad. Sci. USA88:2869-2873.
Colognato-Pyke et al. (1995) J. Biol. Chem. 270:9398-9406.
Colognato et al. (1997) J. Biol. Chem. 272:29330-29336.
Gotwals et al., (1996) J. Clin. Invest. 97:2469-2477.
Green et al. (1994) Nature Genetics 7:13-21.
Hoogenboom et al. (1998) Immunotechnology 4:1-20.
Hoogenboom et al. (2000) Immunol Today 2:371-8.
Huang and Stollar (1991) J. Immunol. Methods 141:227-236.
Keely et al. (1995) J. Cell Sci. 108:595-607.
Kim et al. (2005) J. Biol. Chem. 280:32512-32520.
Knight et al. (2000) J. Biol. Chem. 275-35-40.
Langholz et al. (1995) J.Cell Biol. 131:1903-1915.
Lees et al. (2006) N. Engl. J. Med. 354:588-600.
Persson et al. (1991) Proc. Natl. Acad. Sci USA 88:2432-2436.
Pfaff et al. (1994) Eur. J. Biochem. 225:975-84.
Powers et al. (2001) J. Immunol. Methods 251:123-35.
Riikonen et al. (1995) J. Biol. Chem. 270:1-5.
Tempest et al. (1991) Biotechnology 9:266-271.
Weitz-Schmidt et al. (2001) Nat. Med. 7:687-692.
European Search Report from European Application No. 07784108 dated Nov. 29, 2010.
Go et al., "Antithrombotic Therapy for Stroke Prevention in Atrial Fibrillation", Process in Cardiovascular Diseases, 48(2):108-124 (2005).
U.S. Appl. No. 13/296,778, filed Nov. 15, 2011, Gotwals, Philip.
U.S. Appl. No. 13/297,124, filed Nov. 15, 2011, Karpusas, Michael.
U.S. Appl. No. 13/766,966, filed Feb. 14, 2013, Fowler, Adam Jeremy.
Little, et al., "Of mice and Me: hybridoma and recombant antibodies", Review Immunology Today, vol. 21, No. 8, pp. 364-370, 2000.
Partial European Search Report for EP 02 72 8745 dated Feb. 16, 2005.
Tawil, et al., "Alpha 1 beta 1 integrin heterodimer functions as a dual laminin/collagen receptor in neural cells." Biochemistry. Jul. 10, 1990;29(27):6540-4.
Holmes et al., "Conformational Correction Mechanisms Aiding Antigen Recognition by a Humanized Antibody" J. Exp. Med. 187:479-485 (1998).
Hurtrel et al., "Different Time Course Patterns of Local Expression of Delayed-Typed Hypersensitivity to Sheep Red Blood Cells in Mice" Cell. Immunol. 142:252-263 (1992).
Huth et al., "NMR and Mutagenesis Evidence for an I Domain Allosteric Site that Regulates Lymphocyte Function-Associated Antigen 1 Ligand Binding" Proc. Natl. Acad. Sci. USA 97:5231-5236 (2000).
Ianaro et al., "Anti-Very Late Antigen-1 Monoclonal Antibody Modulates the Development of Secondary Lesion and T-Cell Response in Experimental Arthritis" Lab. Invest. 80:73-80 (2000).
Ignatius et al., "Molecular Cloning of the Rat Integrin alphal Subunit: A Receptor for Laminin and Collagen" J.Cell Biology 111:709-720 (1990).
International Search Report dated Feb. 24, 2004 from International Application No. PCT/US02/11521.
International Search Report dated Nov. 13, 2000 from International Application No. PCT/US00/15004.
International Search Report for PCT/07/69654 dated Oct. 23, 2007.
International Search Report for PCT/US2012/032590 dated Jul. 23, 2012.
Jones et al., "Principles of Protein-Protein Interactions" Proc. Natl. Acad. Sci. USA 93: 13-20 (1996).
Jones et al., "Replacing the Complementarity-Determining Regions in a Human Antibody with Those from a Mouse" Nature 321:522-525 (1986).

(56) References Cited

OTHER PUBLICATIONS

Jordi, "Integrin-collagen complex: a metal glutamate handshake" Structure 8(6):RI21-RI26 (2000).
Kakimoto et al., "The Effect of Anti-adhesion Molecule Antibody on the Development of Collagen-Induced Arthritis" Cell Immunol. 142:326-337 (1992).
Kamata et al., "Critical Threonine and Aspartic Acid Residues within the I Domains of beta 2 Integrins for Interactions with Intercellular Adhesion Molecule 1 (ICAM-1) and C3bi" J. Biological Chem. 270:12531-12535 (1995).
Karpusas et al., "Crystal Structure of the a1b1 Integrin I Domain in Complex with an Antibody Fab Fragment" J. Mol. Biol. 327:1031-1041 (2003).
Kern et al., "The Role of the I Domain in Ligand Binding of the Human Integrin alpha 1 beta1" J. Biol. Chem. 269:22811-55816 (1994).
Kinashi et al., "Adhesion Molecules in Hematopoietic Cells" Blood Cells 20:25-44 (1994).
King et al., "Echovirus 1 Interaction with the Human Very Late Antigen-2 (Integrin) Domain" J. Biol. Chem. 272:28518-285222 (1997).
Kolbinger et al., "Humanization of a Mouse Anti-human IgE Antibody: A Potential Therapeutic for IgE-mediated Allergies" Protein Eng. 6:971-980 (1993).
Krieglstein et al., "Collagen-binding integrin . . . experimental colitis", J. Clin. Invest., 110(12), 1773-1782, 2002.
Laffon et al., Very Late Activation Antigen of Synovial Fluid T cells from Patients with Rheumatoid Arthritis and other Rheumatic Diseases Arthritis and Rheumatism 32:386-392 (1989).
Larson et al., "Primary Structure of the Leukocyte Function-associated Molecule-1 alpha Subunit: an Integrin with an Embedded Domain Defining a Protein Superfamily" J. Cell Biol. 108:703-712 1989.
Lee et al., "Crystal Structure of the A Domain from the Subunit of Integrin CR3 (CD11b/CD18)" Cell 80:631-638 (1995).
Lee et al., "Two conformations of the integrin A-domain (I-domain): a pathway for activation" Structure 3:1333-1340 (1995).
Leibiger et al., "Variable domain-linked oligosaccharides of a human monoclonal IgG: structure and influence on antigen binding", Biochem. J. (1999) 338:529-538.
Li et al., "Three-Dimensional Structures of the Free and Antigen-Bound Fab from Monoclonal Antilysozyme Antibody HyHEL-63" Biochemistry 39:6296-6309 (2000).
Lin et al., "Very late antigen 4 (VLA4) antagonists as anti-inflammatory agents", Current Opinion in Chem. Biology, 2, 453-457, 1998.
Lobb et al., "The Pathophysiologic Role of a4 Integrins In Vivo", J. Clin. Invest., 94, 1722-1728, 1994.
Lobb et al., "The role of a4 Integrins in lung pathophysiology", European Resp. Journ. Supp., 9(22), 1996.
Lowry et al., "Protein Measurement with the folin phenol reagent*" Dept. of Pharma., Washington Univ. School of Med. 265-275 (1951).
Luque et al., "Functional regulation of the human integrin VLA-1 (CD49a/CD29) by divalent cations and stimulatory b1 antibodies", FEBS Letters 346 (1994) 278-284.
Mackay et al., "Lymphotoxin Receptor Triggering Induces Activation of the Nuclear Factor B Transcription Factor in Some Cell Types" J. Biol. Chem. 271 :24934-24938 (1996).
Mendez et al., "Functional Transplant of Megabase Human Immunoglobulin Loci Recapitulates Human Antibody Response in Mice" Nature Genetics 15:146-156 (1997).
Mendrick et al., "Glomerular Epithelial and Mesangial Cells Differentially Modulate the Binding Specificities of VLA-I and VLA-2" Laboratory Investigation 72:367-375 (1995).
Mendrick et al., "Temporal Expression of VLA-2 and Modulation of its ligand Specificity by Rat Glomerular Epithelial Cells in vitro" Lab. Invest. 69:690-702 (1993).
Michishita et al., "A Novel Divalent Cation-Binding Site in the A Domain of the Beta2 Integrin CR3 (CD11b/CDl8) is Essential for Ligand Binding" Cell Press 72:857-867 (1993).
Miyake et al., "Evidence for a Role of the Integrin VLA-4 in Lympho-hemapoiesis" J. Exp. Med. 173:599-607 (1991).
Miyake et al., "Integrin-mediated interaction with Extracellular Matrix Proteins Regulates Cytokine Gene Expression in Synovial Fluid Cells of Rheumatoid Arthritis Patients" J. Exp. Med. 177:863-868 (1993).
Mombaerts et al., "RAG-I-Deficient Mice Have No Mature Band T Lymphocytes" Cell 68:869-877—1992.
Mori et al., "Attenuation of Collagen-Induced Arthritis in 55-kDa TNF Receptor Type 1 (TNFRI)—IgGl-Treated and TNFRI-Deficient Mice" J. Immunol. 157:3178-3182 (1996).
Muller et al., "VEGF and the Fab Fragment of a Humanized Neutralizing Antibody: Crystal Structure of the Complex at 2.4 A Resolution and Mutational Analysis of the Interface" Structure 6:1153-1167 (1998).
Nagler et al., "Reduction in Pulmonary Fibrosis In Vivo by Halofuginone" Am. J. Respir. Crit.Care Med. 154:-1082-1086 (1996).
Nishimura et al., "Integrin-vBeta8" J. Biol. Chem. 269:28708-28715 (1994).
Nolte et al., "Crystal Structure of the Integrin I-Domain: Insights into Integrin I-Domain Function" FEBS Lett. 452:379-385 (1999).
Noto et al., "Identification and Functional Characterization of Mouse CD29 with a mAB" Int. Immunol. 7:835-842 (1995).
Odum, N. et al., "Prevalence of late stage T cell activation antigen (VLA-1) in active juvenile chronic arthritis", Ann. Rheumatic Diseases, 46:846-852, 1987.
Orlandi, "Cloning immunoglobulin variable domains for expression by the polymerase chain reaction" Proc. Natl., Acad. Sci. USA 86:3833-3837 (1989).
Padlan, E.A., "Anatomy of the antibody molecule", Mol Immunol. (1994), 31(3):169-217.
Panka et al., "Variable region framework differences result in decreased or increased affinity of variant anti-digoxin antibodies" Proc. Natl. Acad. Sci. USA 85(9):3080-3084 (1988).
Papadopoulos et al., "Expression of Integrins in Alveolar Epithelia of Fetal and Adult Lung Tissue and in Interstitial Lung Diseases", Verh. Dtsch. Ges. Path., 77, 292-295 (1993). Abstract Only.
Partial European Search Report for EP 02 72 8745 dated Dec. 13, 2004.
Pischel et al., "Use of the monoclonal antibody 12F1 to Characterize the Differentiation Antigen VLA-21" J. Immunol. 138:226-233 (1987).
Plows et al., "Mice Lacking Mature T and B Lymphocytes Develop Arthritic Lesions After Immunization with Type II Collagen" J. Immunol. 162:1018-1023 (1999).
Portolano et al., "Lack of promiscuity in autoantigen-specific H and L chain combinations as revealed by human H and L chain "roulette"", J. Immunol. (1993), 150(3):880-887.
Pozzi et al., "Integrin a1ß1 Mediates a Unique . . . In Vivo", Journal of Cell Biology, 142(2), 587-594, 1998.
Qu et al., "The role of the divalent cation in the structure of the I domain from the CDIIA/CD18 integrin" Structure 4:931-942 (1996).
Qu et al., Crystal structure of the I-domain form the CDIIa1CDI8 (LFA-I, aLbeta2) integrin Proc. Natl. Acad. Sci. USA 92:10277-10281 (1995).
Queen et al., "A humanized antibody that binds to the interleukin 2 receptor" Proc. Natl. Acad. Sci.USA 86:10029-10033 (1989).
Rich et al., "Trench-shaped Binding Sites Promote Multiple Classes of Interactions between Collagen and the Adherence Receptors, 1 Integrin and *Staphylococcus aureus* can MSCRAMM" J. Biol. Chem. 274:24906-24913 (1999).
Riechmann et al., "Reshaping human antibodies for therapy" Nature 332:323-327 (1988).
Riikonen et al., "Transforming growth factor-beta regulates collagen gel contraction by increasing alpha 2 beta 1 integrin expression in osteogenic cells" J. Biol. Chem. 270:376-382 (1994).
Roy-Chaudhury et al., "Adhesion molecule interactions . . . tubulointerstitium", Kidney International, 49, 127-134, 1996.

(56) References Cited

OTHER PUBLICATIONS

Sampson et al., "Global Gene Expression Analysis Reveals a Role for the Integrin in Renal Pathogenesis" J. Biol. Chem. 276:34182-34188 (2001).
Sanchez-Madrid et al., "Three distinct antigens associated with human T-lymphocyte-mediated cytolysis: LFA-1, LFA-2, and LFA-3." Immunol. 79:7489-7493 (1982).
Scheynius et al., "Reduced Contact Sensitivity Reactions in Mice Treated with Monoclonal Antibodies to Leukocyte Function-Associated Molecule-I and intercellular Adhesion Molecule-I" J. Immunol. 150:655-663 (1993).
Schwartz, B.R. et al., "Identification of Surface Proteins Mediating Adherence of CD11/CD18-deficient Lymphoblastoid Cells to Cultured Human Endothelium", J. Clin. Invest., 85:2019-2022, 1990.
Seiffge, "Protective Effects of Monoclonal Antibody to VLA-4 on Leukocyte Adhesion and Course of Disease in Adjuvant Arthritis in Rats" J. Rheumatol. 23:2086-2091 (1996).
Shakin-Eshleman et al., "The Amino Acid at the X Position of an Asn-X-Ser Sequon is an Important Determinant of N-Linked Core-glycosylation Efficiency", J. Biol. Chem. (1996), 271(11), 6363-6366.
Shaw et al., "Molecular Cloning of the Human Mucosal Lymphocyte Integrin alphaE Subunit" J. Biol. Chem. 269:6016-6025 (1994).
Shimaoka, "Computational Design of an Integrin I Domain, etc." Nature Structural Biol. 7(8):674-678 (2000).
Sonnenberg et al., "A Complex of Platelet Glycoproteins Ie and IIa Identified by a Rat Monoclonal Antibody" J. Biol. Chem. 262:10376-10383 (1987).
Springer et al., "Adhesion receptors of the immune system" Nature 346:425-434 (1990).
Stacker et al., "Leukocyte integrin P150,95 (CD11c/CD18) functions as an adhesion molecule binding to a counter-receptor on stimulated endothelium" J. Immunol., 146:648-655 (1991).
Suzuki, K. et al., "Semaphorin 7A initiates T-cell-mediated inflammatory responses through $a1\beta1$ integrin", Nature, 446:680-684, 2007.
Takada et al., "The primary structure of the VLA-2/Collagen receptor alpha 2 subunit (platelet GPIa): homology to other integrins and the presence of a possible collagen-binding domain" J. Cell Biol. 109:397-407 (1989).
Taylor et al., "Transfer of Type II Collagen-Induced Arthritis From DBAII to Severe Combined Immunodeficiency Mice can be Prevented by Blockage of Mac-I" Immunology 88: 315-321 (1996).
Tedder et al., "L-Selectin-deficient Mice Have Impaired Leukocyte Recruitment into Inflammatory Sites" J. Exp. Med. 181:2259-2264 (1995).
Terashita et al., "Enhancement of Delayed-Type Hypersensitivity to Sheep Red Blood Cells in Miche by Granulocyte Colony-Stimulating Factor Administration at the Elicitation Phase" J. Immunol. 156:4638-4643 (1996).
Terato et al., "Collagen-Induced Arthritis in Mice: Synergistic Effect of *E. coli* Lipopolysaccharide Bypasses Epitope Specificity in the Induction of Arthritis with Monoclonal Antibodies to Type II Collagen" Autoimmunity 22: 137-147 (1995).
Terato et al., "Induction of Arthritis with Monoclonal Antibodies to Collagen" J. Immunol. 148:2103-2108 (1992).
Tomizuka et al., "Functional Expression of Germline Transmission of a Human Chromosome Fragment in Chimaeric Mice" Nature Genetics 16:133-143 (1997).
Tsunoda, I. et al., "Modulation of Experimental Autoimmune Encephalomyelitis by VLA-2 Blockade", Brain Pathol., 17:45-55, 2007.
Van der Vieren et al., A Novel Leukointegrin alphadbeta2, Binds Preferentially to ICAM-3 Immunity 3:683-690 (1995).
Verhoeyen et al., "Reshaping Human Antibodies: Grafting an Antilysozyme Activity" Science 239:1534:1536 (1987).
Wang et al., "Differential regulation of airway epithelial integrins by growth factors" Am. J. Respir.Cell Mol. Biol. 15:664-672 (1996).
Ward et al., "Binding activities of a repertoire of single immunoglobulin variable domains secreted from *Escherichia coli*" Nature 341:544-546 (1989).
Watts, G.M., et al., "Manifestations of Inflammatory Arthritis are Critically Dependent on FLA-1 superscript 1", J. Immunology, 174:3668-3675, 2005.
Wayner et al., "The function of multiple extracellular matrix receptors in mediating cell adhesion to extracellular matrix: preparation of monoclonal antibodies to the fibronectin receptor that specifically inhibit cell adhesion to fibronectin and react with platelet glycoproteins Ic-IIa" J. Cell Biol. 107:1881-1891 (1988).
Weinacker et al., "Role of the Integrin alphavbeta6 in Cell Attachment to Fibronectin" J. Biol.Chem. 269:6940-6948 (1993).
Welschof et al., "Amino Acid Sequence based PCR Primers for Amplification of Rearranged Human Heavy and Light Chain Immunoglobulin Variable Region Genes" J. Immuno. Meth. 179:203-214 (1995).
Woessner et al., "The determination of hydroxyproline in tissue and protein samples containing small proportions of this imino acid" Arch. Biochem. Biophys. 93:440-447 (1961).
Wright, A. and Morrison, S.L., Effect of Altered CH2-associated Carbohydrate Structure on the Functional Properties and In Vivo Fate of Chimeric Mouse-Human Immunoglobulin G1, J. Exp. Med. (1994), 180:1087-1096.
Yao et al., "Laminins promote the locomotion of skeletal myoblasts via the alpha 7 integrin receptor" J. Cell Science 109:3139-3150 (1996).
Yednock, T.A. et al., "Prevention of experimental autoimmune encephalomyelitis by antibodies against $a4\beta1$ integrin", Nature, 356:63-66, 1992.
Written Opinion for EP 009426545 dated Mar. 9, 2001.
Written Opinion for PCT/US12/23590 dated Jul. 23, 2012.
International Search Report for PCT/US12/023590 dated Jul. 23, 2012.
Holt et al., "Domain antibodies: proteins for therapy", Trends Biotechnol. 2003; 21(11):484-490. (Abstract Only).
Snyder et al. "The binding conformation of Taxol in b-tubulin: A model based on electron crystallographic density" PNAS, 2001; 98(9) 5312-5316.
International Preliminary Report on Patentability & Written Opinion for PCT/US2007/069654 dated Oct. 10, 2007.
Abraham, et al., "A Monoclonal Antibody to $a1\beta1$ Blocks Antigen-induced Airway Responses in Sheep", Am. J. Respir. Crit. Care Med. Jan. 1, 2004 vol. 169 No. 1 97-104.
Baker, et al., "Developmental and injury-induced expression of $a1\beta1$ and $a6\beta1$ integrins in the rat spinal cord", Brain Res. Jan. 26, 2007; 1130(1): 54-66.
Baldwin et al., "Cation binding to the integrin CDII b I domain and activation model assessment" Structure 6:923-935 (1998).
Bank, I. et al., Analysis of recombinant human a1 integrin I-domain with a function-blocking monoclonal antibody, 1B3.1, IMAJ, vol. 2, Supplement 2, pp. 19-20, Dec. 2000.
Bank, I. et al., "Expression and Functions of Very Late Antigen 1 in Inflammatory Joint Diseases", J. Clin. Immunol. 11(1):29-38, 1991.
Bennett et al., "Inhibition of fibrinogen binding to stimulated human platelets by a monoclonal antibody" Proc. Natl. Acad. Sci.USA 80:2417-2421 (1983).
Border et al., "Transforming Growth Factor Beta in Tissue Fibrosis" New England J. Medicine 331:1286-1292 (1994).
Bossy et al., "Characterization of the Integrin Alpha8 subunit: A new intefrin beta1-associated subunit, which is prominently expressed on axons and on cells in contact with basal laminae in chick embryos" EMBO J. 10:2375-2385 (1991).
Brezinsky et al., "A Simple Method of Enriching Populations of Transfected CHO Cells for Cells of Higher Specific Productivity" J. Immunol. Methods 277:141-155 (2003).
Bridges et al., "Variable Region cDNA Sequences and Characterization of Murine Anti-Human Interferon γ Receptor Monoclonal Antibodies that Inhibit Receptor Binding by Interferon γ" Mol. Immunol. 32:1329-2989 (1995).
Briesewitz, et al., "Expression of Native and Truncated Forms of the Human Integrin a1 Subunit," Journal of Biological Chemistry, 268(4):2989-2996 (1993).

(56) References Cited

OTHER PUBLICATIONS

Camper et al., "Isolation, Cloning, and Sequence Analysis of the Integrin Subunit a10, a Bet1-associated Collagen Binding integrin Expressed on Chondrocytes*" J. Biol. Chem. 273:20383-20389 (1998).
Carter et al., "Humanization of an Anti-p185HER2 Antibody for Human Cancer Therapy" Proc. Natl. Acad. Sci. USA 89:4285-4289 (1992).
Cerf-Bensussan et al., "The human intraepithelial lymphocyte marker HML-1 is an integrin consisting ofa Beta7 subunit associated with a distinctive alpha chain" Eur. J. Immunol. 22:273-277 (1992).
Chapman, et al., "Leukocyte adhesion molecules", British Medical Bulletin, 51(2):296-311, 1995.
Chothia et al., "Conformations of Immunoglobulin Hypervariable Regions" Nature 342:877-883 (1989).
Clackson et al., "Making antibody fragments using phage display libraries" Proc. Natl. Acad. Sci.USA 352:624-628 (1991).
Colbert et al., "The effect of fluorescein labels on the affinity of antisera to small haptens" J. lmunol. Methods 140:227-233 (1991).
Written Opinion European Patent Office for application 04018151.3 dated Mar. 22, 2012.
Cook et al., "Treatment with an Antibody to VLA-1 Integrin Reduces Glomerular and Tubulointerstitial Scarring in a Rat Model of Crescentic Glomerulonaphritis" Am. J. Pathol. 161:1265-1272 (2002).
Corbi et al., "CDNA cloning and complete primary struction for the alpha subunit of a leukocyte adhesion glycoprotein" EMBO Journal, vol. 6, No. 13, p. 4023-4028, 1987.
Corbi et al., The Human Leukocyte Adhesion Glycoprotein Mac-I (Complement Receptor Type 3, CDIIb) alpha Subunit J. Biol. Chem. 263:12403-12411, 1988.
Cosgrove et al., "Integrin and Transforming Growth Factor-I Play Distinct Roles in Alport Glomerular Pathogenesis and Serve as Dual Targets for Metabolic Therapy" Am. J. Path. 157:16498-1659 (2000).
Davies et al., "Interactions of Protein Antigens with Antibodies" Proc. Natl. Acad. Sci. USA 937-12 (1996).
Davies, "The osteoclast Functional Antigen, Implicated in the Regulation of Bone Resorption, Is Biochemically Related to the Vitronectin Receptor" J. Cell Biology 109:1817-1826 (1989).
De Fougerolles et al., "Global Expression Analysis of Extracellular Matrix-Integrin interactions in Monocytes" Immunity 13:749-758 (2000).
De Fougerolles et al., "Regulation of Inflammation by Collagen-Binding Integrins and 1 * in Models of Hypersensitivity and Arthritis" J. Clin. Invest. 105:721-729 (2000).
Diamond et al., "The I Domain is a Major Recognition Site on the Luekocyte lntegrin Mac-1 (CD-11b/CD18) for Four distinct Adhesion Ligands", J. Cell Biology 120:1031-1043 (1993).
Edwards et al., "Identification of Amino Acids in the CDIIa I-domain Important for Binding of the DA Leukocyte Function-associated Antigen-I (LFA-I) to Intercellular Adhesion Molecules-I (ICAM-1)*" J. Biol. Chem. 270:12635-12640 (1995).
Eigenbrot et al., "X-ray Structures of the Antigen-binding Domains from Three Variants of Humanized anti_p185HER2 Antibody 4D5 and Comparison with Molecular Modeling" J. Mol. Biol. 229:969-995 (1993).
Elices, M.J. et al., "VCAM-1 on Activated Endothelium Interacts with the Leukocyte Integrin VLA-4 at a Site Distinct from the VLA-4/Fibronectin Binding Site", Cell, 60:577-584, 1990.
Emsley et al., "Crystal Structure of the I Domain from Integrin" J. Biol. Chem. 272:28512-28517 (1997).
Emsley et al., "Structural Basis of Collagen Recognition by Integrin" Cell 100:47-56 (2000).
EP Search Report & Opinion for EP 10 185 467.7 dated Mar. 2, 2011.
EP Search Report for EP 04 01 8151.3 dated Feb. 17, 2011.
Fabbri et al., "A functional monoclonal antibody recognizing the human alpha1-integrin I-domain" Tissue Antigens 48:47-51 (1996).
Fiorucci et al., "Importance of Innate Immunity and Collagen Binding Integrin a1b1 in TNBS-Induced Colitis", Immunity, 17, 769-780, 2002.
Fischmann et al., "Crystallographic Refinement of the Three-Dimensional Structure of the FabD1.3-Lysozyme Complex at 2.5-Å Resolution" J. Biol. Chem. 266:12915-12920 (1991).
Foote et al., "Antibody Framework Residues Affecting the Conformation of the Hypervariable Loops" J. Mol. Biol. 224:487-499 (1992).
Gardner et al., "Absence of integrin a1β1 in the mouse causes . . . wounded dermis", J. Cell Science, 112, 263-272, 1999.
Gardner et al., "Deletion of Integrin a1 by Homologous . . . Cell Adhesion", Developmental Biology, 175, 301-313, 1996.
Gaspari et al., "Contact Hypersensitivity" Current Protocols in Immunology J.E. Coligan et al., Editors, John Wiley & Sons, New York, Section 4.2.1-4.2.5 (1991).
Gotwals et al., "Divalent Cations Stabilize the a1 β1 Integrin 1 Domain" Biochemistry 38:8280-8288 (1999).
Grayson et al., "Alphabeta2 Integrin is Expressed on Human Eosinophils and Functions as an Alternative Ligand for Vascular Cell Adhesion Molecule 1 (VCAM-I)" J. Exp. Med. 188:2187-2191 (1984).
Hemler et al. "Characterization of the Cell Surface Heterodimer VLA-4 and Related Peptides" J.Immunol. 262:11478-11485 (1987).
Hemler et al., "Glycoproteins of 210,000 and 130,000 M.W. On Activated T Cells: Cell Distribution and Antigenic Relation to Components on Resting Cells and T Cell Lines" J. Imunnol. 132:3011-3018 (1984).
Hemler et al., "Very Late Activation Antigens on Rheumatoid Synovial Fluid T Lymphocytes: Association with Stages of T Cell Activation" J. Clin. Invest. 78:696-702 (1986)
Hemler et al., "VLA-I:A T Cell Surface Antigen which Defines a Novel Late Stage of Human T Cell Activation" Eur. J. Immunol. 15:502-508 (1985).
Hessle et al., "Basement membrane diversity detected by monoclonal antibodies" Differentiation 26:49-54 (1984).
Hokibara et al., "Effects of monoclonal antibodies . . . CBA/J mice", Clin. Exp. Immunol. 114, 236-244, 1998.
International Preliminary Examination Report for PCT/US01/15004 dated Jul. 7, 2001.
International Preliminary Examination Report for PCT/US02/11521 dated Apr. 28, 2004.
International Search Report and Written Opinion, International Application No. PCT/US2013/026034, dated Oct. 21, 2013.
Santarus: "Santarus Initiates Phase I Clinical Study with SAN-300," http://ir.santarus.com/releasedetail.cfm?releaseid+555930, XP002696720, Mar. 11, 2011 [retrieved on May 8, 2012].
Alcocer-Varela, J., et al., "Interleukin-1 and Interleukin-6 Activities are Increased in the Cerebrospinal Fluid of Patients with CNS Lupus Erythematosus and Correlate with Local Late T-Cell Acitvation Markers," Lupus, 1:111-117 (1992).
Schapira, K., et al., "Genetic Deletion or Antibody Blockade of alpha1beta1 Integrin Induces a Stable Plaque Phenotype in ApoE-/- Mice," Arteriosclerosis, Thrombosis, and Vascular Biology, 25:1917-1924 (2005).
Senger, D.R., et al., "The alpha1beta1 and alpha2beta1 Integrins Provide Critical Support for Vascular Endothelial Growth Factor Signaling, Endothelial Cell Migration, and Tumor Angiogenesis," American Journal of Pathology, 160(1):195 (2002).
U.S. Appl. No. 11/108,581, Granted, filed Apr. 18, 2005, U.S. Pat. No. 7,462,353, Dec. 9, 2008.
U.S. Appl. No. 12/268,459, Granted, filed Nov. 11, 2008, U.S. Pat. No. 8,084,031, Dec. 27, 2011.
U.S. Appl. No. 13/296,778, Granted, filed Nov. 15, 2011, U.S. Pat. No. 8,557,240, Oct. 15, 2013.
U.S. Appl. No. 14/021,547, Published, filed Sep. 9, 2013, 2014-0154259.
U.S. Appl. No. 09/996,738, Granted, filed Jun. 1, 2000, U.S. Pat. No. 6,955,810, Oct. 18, 2005.
U.S. Appl. No. 12/015,213, Granted, filed Jan. 16, 2008, U.S. Pat. No. 7,723,073, May. 25, 2010.
U.S. Appl. No. 13/017,919, Granted, filed Jan. 31, 2011, U.S. Pat. No. 8,084,028, Dec. 27, 2011.

(56) References Cited

OTHER PUBLICATIONS

U.S. Appl. No. 13/297,124, Published, filed Nov. 15, 2011, 2012-0177638.
U.S. Appl. No. 12/727,965, Granted, filed Mar. 189, 2010, U.S. Pat. No. 7,910,099, Mar. 22, 2011.
U.S. Appl. No. 14/597,262, Pending, filed Jan. 15, 2015.
U.S. Appl. No. 10/474,832, Granted, filed Apr. 12, 2002, U.S. Pat. No. 7,358,054, Apr. 15, 2008.
U.S. Appl. No. 13/981,699, Published, filed Feb. 2, 2012, 2014-0017261.
U.S. Appl. No. 13/766,966, Published, filed Feb. 14, 2013, 2013-0216556.
U.S. Appl. No. 14/015,039, Abandoned, filed Aug. 30, 2013, 2014-0110827.
U.S. Appl. No. 14/379,095, Pending, filed Feb. 14, 2013.
Adams et al., "Coronary Risk Evaluation in Patients with Transient Ischemic Attack and Ischemic Stroke" Circulation, 108(9):1278-1290 (2003).
Bank I et al., "A novel monoclonal antibody, 1B3.1, binds to a new epitope of the VLA-1 molecule", Cellular Immunology, 122:416-423 (1989).
Edmundson et al. "Binding of peptides to proteins: an exercise in molecular design." Ciba Found Symp. 158: 213-25, (1991), Abstract.
Extended European Search Report for EP 14178388.6 dated Jan. 27, 2015.
International Preliminary Report on Patentability for International Application No. PCT/US2013/026034 dated Aug. 19, 2014.
Nienaber VL et al., "Discovering novel ligands for macromolecules using X-ray crytallographic screening", Nature Biotechnology, 18; 1105-1108, (2000).
Solenski et al., "Transient Ischemic Attacks: Part II. Treatment" American Family Physician, 69(7):1681-1688 (2004).
Van Regenmortel, Mapping Epitope Structure and Activity: From One-Dimensional Prediction to Four-Dimensional Description of Antigenic Specificity, Methods: A Comparaion to Methods in Enzymology, 9, 465-472 (1996).
Weinachter et al., "Group Report 8: Models of Hypoxia and Cerebral Ischemia", Pharmacopsychiat, 23, 94-98, (1990).
Diffuse Connective Tissue Disease: Rheumatoid Arthritis, The Merk Manual, 17th Edition, 1999, pp. 416-423.
Extended European Search Report for EP 12742734.2 dated Apr. 20, 2015.
Morand et al.: "Continuation of long term treatment with hydroxychloroquine in systemic lupus erythematosus and rheumatoid arthritis", Annals of the Rheumatic Diseases, 1992, 51: 1318-1321.
Patient Information on Etanercept, Australian Rheumatology Association, Revised May 2009—next review May 2010, pp. 1-3.
Rubbert-Roth et al.: "Treatment options in patients with rheumatoid arthritis failing intial TNF inhibitor therapy: a critical review", Arthritis Research & Therapy, 2009, 11 (Suppl 1): S1, pp. 1-12.

* cited by examiner

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Gln Arg Gly Gly Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 2

Gly Phe Pro Gly Glu Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Hydroxyproline

<400> SEQUENCE: 3

Gly Arg Pro Gly Glu Arg
1               5
```

METHODS OF TREATING STROKE AND TRAUMATIC BRAIN INJURY USING HUMANIZED AQC2 ANTI-VLA-1 ANTIBODIES

CROSS-REFERENCE TO RELATED APPLICATION

This application claims the benefit of U.S. Provisional Application No. 60/809,149, filed May 25, 2006, which is hereby incorporated by reference in its entirety.

BACKGROUND

Stroke is a leading cause of death and disability worldwide. About 700,000 Americans will have a stroke this year. In the United States, stroke is the third most-frequent cause of death and a leading cause of severe, long-term disability.

SUMMARY

The invention is based, in part, on the observation that modulation of VLA-1 can be used to treat an ischemic injury, e.g., stroke. Accordingly, in one aspect, the invention provides methods of treating stroke in a subject. The method includes administering to the subject a VLA-1 antagonist in an amount effective to treat stroke. A "VLA-1 antagonist" refers to an agent (e.g., any compound) that at least partially inhibits an interaction or activity of VLA-1. For example, the agent at least partially inhibits an activity of VLA-1 (e.g., binding of VLA-1 to a ligand, e.g., collagen), or the agent at least partially inhibits a nucleic acid encoding VLA-1, e.g., to reduce VLA-1 protein expression. In one embodiment, the agent reduces the ability of VLA-1 to bind to collagen, e.g., collagen IV, e.g., reduces affinity of VLA-1/collagen binding by a factor of at least 2, 3, 5, 10, 20, 50, or 100, and/or reduces VLA-1/collagen binding by at least 5%, e.g., at least 10%, 25%, 50%, 75%, 90%, 95%, or more, as compared to the binding in the absence of the agent.

In one embodiment, the VLA-1 antagonist is an anti-VLA-1 antibody, or antigen-binding fragment thereof. The anti-VLA-1 antibody can be a monoclonal antibody, or an antigen-binding fragment thereof. The anti-VLA-1 antibody can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')$_2$ or scFv fragment, or one or more CDRs). An antibody, or antigen-binding fragment thereof, can include two heavy chain immunoglobulins and two light chain immunoglobulins, or can be a single chain antibody. The antibody can, optionally, include a constant region chosen from a kappa, lambda, alpha, gamma, delta, epsilon or a mu constant region gene. In some embodiments, the anti-VLA-1 antibody includes a heavy and light chain constant region substantially from a human antibody, e.g., a human IgG1 constant region or a portion thereof. In some embodiments, the anti-VLA-1 antibody is a human antibody.

In other embodiments, the antibody, or antigen-binding fragment thereof, is a chimeric or humanized antibody. As discussed herein, the antibodies can be CDR-grafted, humanized, or more generally, antibodies having CDRs from a non-human antibody and a framework that is selected as less immunogenic in humans, e.g., less antigenic than the murine framework in which a murine CDR naturally occurs.

In a preferred embodiment, the anti-VLA-1 antibody is a non-naturally occurring antibody, e.g., a chimeric, CDR-grafted, or humanized antibody having at least heavy chain CDR3, and preferably all heavy chain CDRs, more preferably all three heavy chain CDRs and all three light chain CDRs from a nonhuman antibody, e.g., a nonhuman antibody described herein. In a preferred embodiment, the CDRs can differ from a CDR referred to herein by 1, 2 or 3 amino acid residues, e.g., heavy chain CDR3 can be from a source described herein but otherwise another CDR can vary as described herein.

Preferred anti-VLA-1 antibodies include, e.g., a humanized AQC2 antibody (e.g., produced by a hybridoma having ATCC Deposit No. PTA-3274), AJH10 (ATCC PTA-3580), hAQC2 (ATCC PTA-3275), haAQC2 (ATCC PTA-3274), hsAQC2 (ATCC PTA-3356), mAQC2 (ATCC PTA-3273), and monoclonal antibody 1B3 (ATCC HB-10536). In some embodiments, the anti-VLA-1 antibody can bind to the same epitope as AQC2, AJH10, hAQC2, haAQC2, hsAQC2, mAQC2, and/or 1B3. In some embodiments, the anti-VLA-1 antibody competes with AQC2, AJH10, hAQC2, haAQC2, hsAQC2, mAQC2, and/or 1B3 for binding to VLA-1.

In some embodiments, the anti-VLA-1 antibody binds to the α1 subunit of VLA-1, e.g., the α1-I domain of VLA-1.

In one embodiment, the VLA-1 antagonist is a polypeptide, e.g., laminin or collagen I, III or IV, or a VLA-1 binding peptide of laminin or collagen I, III or IV described herein. In one embodiment, the VLA-1 antagonist is a VLA-1 peptide, e.g., a fragment of the α1 subunit, e.g., a fragment of the α1-1 domain containing the amino acid sequence VQRGGR (SEQ ID NO: 1) or a similar amino acid sequence with conservative amino acid substitutions. The laminin, collagen or VLA-1 peptides block VLA-1 function as tested by, e.g., its ability to inhibit K562-α1 dependent adhesion to collagen IV as described herein.

In one embodiment, the VLA-1 antagonist is an inhibitor of the expression or translation of an VLA-1 nucleic acid, such as a double-stranded RNA (dsRNA) molecule, an antisense molecule, a ribozyme, a triple helix molecule, aptamer, or any combination thereof.

In one embodiment, the VLA-1 antagonist is a small molecule described herein (e.g., a chemical agent having a molecular weight of less than 2500 Da, preferably, less than 1500 Da), or a chemical, e.g., a small organic molecule.

In one embodiment, the VLA-1 antagonist can be administered in an amount and/or for a time sufficient to reduce ischemic damage in neuronal tissue in the brain.

The subject is typically a mammal, e.g., human, dog, cat, monkey, rabbit, or agriculture mammal (e.g., horse, cow, pig, and so on). For example, the subject is a human, e.g., a human male or female. The subject can be at least 18, 25, 30, 45, 50, 55, 60, or 70 years old.

In one embodiment, the subject has experienced a stroke. The stroke can be a hemorrhagic stroke, ischemic stroke, or a transient ischemic attack (TIA).

In one embodiment, the subject has experienced a stroke within 48 hours, e.g., within 2, 3, 5, 8, 12, 20, or 30 hours of treatment. In another embodiment, the subject has experienced a stroke more than 48 hours before, but within the last three or two weeks, of treatment.

In another embodiment, the subject is at risk for stroke, e.g., has experienced or is experiencing conditions that create a risk for stroke. Examples of such conditions include high blood pressure; tobacco use; diabetes mellitus; carotid or other artery disease; peripheral artery disease; atrial fibrillation; other heart disease; transient ischemic attacks (TIAs); certain blood disorders (e.g., high red blood cell count; Sickle cell disease); high blood cholesterol; physical inactivity and obesity; excessive alcohol; some illegal drugs; a prior stroke; or prior heart attack.

In one embodiment, the subject exhibits one or more of the following symptoms: sudden numbness or weakness of the face, sudden numbness or weakness of an arm; sudden numbness or weakness of a leg; sudden confusion; sudden trouble speaking; sudden trouble understanding; sudden trouble seeing in one or both eyes; sudden trouble walking; sudden dizziness; sudden loss of balance or coordination; sudden and severe headache with no known cause. In some embodiments, the subject has been diagnosed as having sustained a stroke.

In one embodiment, the VLA-1 antagonist is administered in an amount sufficient to reduce infarct size, e.g., by at least 5, 10, 15, 20, 40, 50, 60, 70, or 80% or more, in neuronal tissue in the brain, relative to the infarct size in an untreated subject. The amount sufficient to reduce infarct size can be evaluated using an animal model, e.g., as described herein.

In one embodiment, the VLA-1 antagonist is administered in an amount sufficient to improve symptoms in one or more stroke assessment criterion, e.g., a criterion or scale described herein, by at least 5, 10, 15, 20, 40, 50, 60, 70, or 80% or more, or by a half-step or full step in the scale. For example, modified Rankin scale score can be reduced by at least 1 step, e.g., by at least 2, 3 or 4 steps, and/or the score can be decreased to, e.g., 4, 3, 2, 1 or 0. NIHSS score can be reduced by at least 1 step, e.g., by at least 2, 3, 4, 5, 6, 7, 8, 9, 10, 12, 14, 16, 18, 20 steps or more, and/or the score can be decreased to, e.g., 15, 13, 12, 10, 9, 8, 7, 6, 5, 4, 3, 2, 1 or 0. Barthel index score can be increased by at least 5 steps, e.g., at least 10, 15, 20, 25, 30, 35, 40, 45, 50, 55, 60 steps or more, and/or the score can be increased to, e.g., 50, 60, 70, 75, 80, 85, 90, 95 or 100.

In one embodiment, the VLA-1 antagonist is administered at a dosage of 0.025 mg/kg per day to 30 mg/kg per day, e.g., 0.1 to 5 mg/kg, e.g., 0.3 to 3 mg/kg. In one embodiment, the VLA-1 antagonist is administered at least twice within a 14 day period after a stroke, e.g., at least 3, 4, 5, 6, 7, 8, 9, 10, 11, 12, 13 or 14 times within a 14 day period after a stroke. The antagonist can be administered, for example, once daily, once every other day, twice a week, once a week, or once per day for 1 day, e.g., for 2, 3, 4, 5, 6, 7, 14 or 28 days. The VLA-1 antagonist can be administered intravenously or parenterally.

In one embodiment, the VLA-1 antagonist is administered in combination with a treatment for stroke. For example, the treatment includes administering a second agent that provides a therapeutic benefit to a patient who has or is at risk for stroke. Exemplary second agents include, e.g., a thrombolytic agent (e.g., streptokinase, acylated plasminogen-streptokinase activator complex (APSAC), urokinase, single-chain urokinase-plasminogen activator (scu-PA), anti-inflammatory agents, thrombin-like enzymes from snake venoms such as ancrod, thrombin inhibitors, tissue plasminogen activator (t-PA) and biologically active variants of each of the above); an anticoagulant (e.g., warfarin or heparin); antiplatelet drug (e.g., aspirin); a glycoprotein IIb/IIIa inhibitor; a glycosaminoglycan; coumarin; GCSF; melatonin; an apoptosis inhibitor (e.g., caspase inhibitor), an anti-oxidant (e.g., NXY-059); and a neuroprotectant (e.g., an NMDA receptor antagonists or a cannabinoid antagonist).

In a preferred embodiment, the VLA-1 antagonist and the second agent are administered at the same time. In a preferred embodiment, the VLA-1 antagonist is administered first in time and the second agent is administered second in time. In a preferred embodiment, the second agent is administered first in time and the VLA-1 antagonist is administered second in time.

As used herein, "administered in combination" means that two or more agents (e.g., the VLA-1 antagonist and the second agent) are administered to a subject at the same time or within an interval, such that there is overlap of an effect of each agent on the patient. Preferably the administrations of the first and second agent are spaced sufficiently close together such that a combinatorial effect is achieved. The interval can be an interval of hours, days or weeks. Generally, the agents are concurrently bioavailable, e.g., detectable, in the subject. In a preferred embodiment at least one administration of one of the agents, e.g., the first agent, is made while the other agent, e.g., the VLA-1 antagonist, is still present at a therapeutic level in the subject.

In one embodiment, the method also includes evaluating the subject for a post-stroke criterion, e.g., a stroke assessment criterion or scale described herein. In some embodiments, the evaluation is performed at least 1 hour, e.g., at least 2, 4, 6, 8, 12, 24, or 48 hours, or at least 1 week, 2 weeks, 4 weeks, 10 weeks, 13 weeks, 20 weeks or more, after the administration of the VLA-1 antagonist. The subject can be evaluated in one or more of the following periods: prior to beginning of treatment; during the treatment; or after one or more elements of the treatment have been administered. Evaluating can include evaluating the need for further treatment with the same VLA-1 antagonist or for additional treatment with additional agents. In a preferred embodiment, if a preselected outcome of the evaluation is obtained, an additional step is taken, e.g., the subject is administered another treatment or another evaluation or test is performed.

In another embodiment, the method further includes a step of identifying a subject who has a stroke (e.g., ischemic stroke, hemorrhagic stroke, or transient ischemic attack) or symptoms of a stroke.

In one aspect, the disclosure features a method of treating a subject, the method including (a) determining if a patient has ischemia, e.g., post-stroke ischemia; (b) determining if stroke or other event causing ischemia is within a preselected time, e.g., a time described herein; and, if (a) and (b) are satisfied, administering to the subject a VLA-1 antagonist in an amount effective to treat the ischemia.

In one aspect, the disclosure features a VLA-1 antagonist for use in treating stroke, e.g., as described herein. The antagonist can be a VLA-1 antagonist described herein, e.g., a VLA-1 antibody described herein. In another aspect, the disclosure features the use of a VLA-1 antagonist for the manufacture of a medicament for treating stroke, e.g., as described herein. The antagonist can be a VLA-1 antagonist described herein, e.g., a VLA-1 antibody described herein.

In one aspect, the disclosure features a container that includes a VLA-1 antagonist, e.g., a VLA-1 antibody, and a label with instructions for use of the antagonist in treating stroke.

In one aspect, the disclosure features methods for treating an ischemic injury in a subject, e.g., an ischemic injury described herein, the method including administering to the subject a VLA-1 antagonist, e.g., an anti-VLA-1 antibody described herein, in an amount effective to treat the ischemic injury. In another aspect, the disclosure features methods for treating ischemia-reperfusion injury in a subject, the method including administering to the subject a VLA-1 antagonist, e.g., an anti-VLA-1 antibody described herein, in an amount effective to treat the ischemia-reperfusion injury.

In another aspect, the disclosure features methods of treating traumatic brain injury (TBI) in a subject. The method includes administering to the subject a VLA-1 antagonist in an amount effective to treat TBI.

In one embodiment, the VLA-1 antagonist is an anti-VLA-1 antibody, or antigen-binding fragment thereof. The anti-VLA-1 antibody can be a monoclonal antibody, or an antigen-binding fragment thereof. The anti-VLA-1 antibody can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, F(ab')$_2$ or scFv fragment, or one or more CDRs). An antibody, or antigen-binding fragment thereof, can include two heavy chain immunoglobulins and two light chain immunoglobulins, or can be a single chain antibody. The antibody can, optionally, include a constant region chosen from a kappa, lambda, alpha, gamma, delta, epsilon or a mu constant region gene. In some embodiments, the anti-VLA-1 antibody includes a heavy and light chain constant region substantially from a human antibody, e.g., a human IgG1 constant region or a portion thereof. In some embodiments, the anti-VLA-1 antibody is a human antibody.

In other embodiments, the antibody, or antigen-binding fragment thereof, is a chimeric or humanized antibody. As discussed herein, the antibodies can be CDR-grafted, humanized, or more generally, antibodies having CDRs from a non-human antibody and a framework that is selected as less immunogenic in humans, e.g., less antigenic than the murine framework in which a murine CDR naturally occurs.

In a preferred embodiment, the anti-VLA-1 antibody is a non-naturally occurring antibody, e.g., a chimeric, CDR-grafted, or humanized antibody having at least heavy chain CDR3, and preferably all heavy chain CDRs, more preferably all three heavy chain CDRs and all three light chain CDRs from a nonhuman antibody, e.g., a nonhuman antibody described herein. In a preferred embodiment, the CDRs can differ from a CDR referred to herein by 1, 2 or 3 amino acid residues, e.g., heavy chain CDR3 can be from a source described herein but otherwise another CDR can vary as described herein.

Preferred anti-VLA-1 antibodies include, e.g., a humanized AQC2 antibody (e.g., produced by a hybridoma having ATCC Deposit No. PTA-3274), AJH10 (ATCC PTA-3580), hAQC2 (ATCC PTA-3275), haAQC2 (ATCC PTA-3274), hsAQC2 (ATCC PTA-3356), mAQC2 (ATCC PTA-3273), and monoclonal antibody 1B3 (ATCC HB-10536). In some embodiments, the anti-VLA-1 antibody can bind to the same epitope as AQC2, AJH10, hAQC2, haAQC2, hsAQC2, mAQC2 and/or 1B3. In some embodiments, the anti-VLA-1 antibody competes with AQC2, AJH10, hAQC2, haAQC2, hsAQC2, mAQC2 and/or 1B3 for binding to VLA-1.

In some embodiments, the anti-VLA-1 antibody binds to the α1 subunit of VLA-1, e.g., the α1-I domain of VLA-1.

In one embodiment, the VLA-1 antagonist is a polypeptide, e.g., laminin or collagen I, III or IV, or a VLA-1 binding peptide of laminin or collagen I, III or IV described herein. In one embodiment, the VLA-1 antagonist is a VLA-1 peptide, e.g., a fragment of the α1 subunit, e.g., a fragment of the α1-I domain containing the amino acid sequence VQRGGR (SEQ ID NO: 1) or a similar amino acid sequence with conservative amino acid substitutions. The laminin, collagen or VLA-1 peptides block VLA-1 function as tested by, e.g., its ability to inhibit K562-α1 dependent adhesion to collagen IV as described herein. In one embodiment, the VLA-1 antagonist is an inhibitor of the expression or translation of a VLA-1 nucleic acid, such as a double-stranded RNA (dsRNA) molecule, an antisense molecule, a ribozyme, a triple helix molecule, aptamer, or any combination thereof.

In one embodiment, the VLA-1 antagonist is a small molecule described herein (e.g., a chemical agent having a molecular weight of less than 2500 Da, preferably, less than 1500 Da), or a chemical, e.g., a small organic molecule.

In one embodiment, the VLA-1 antagonist can be administered in an amount and/or for a time sufficient to treat TBI, e.g., to cure, heal, alleviate, relieve, alter, remedy, ameliorate, improve or affect TBI, e.g., one or more symptoms of TBI described herein.

The subject is typically a mammal, e.g., human, dog, cat, monkey, rabbit, or agriculture mammal (e.g., horse, cow, pig, and so on). For example, the subject is a human, e.g., a human male or female. The subject can be at least 18, 25, 30, 45, 50, 55, 60, or 70 years old.

The TBI can be, e.g., a contusion, bruise, laceration or hematoma. In some embodiments, the VLA-1 antagonist is administered to treat a primary TBI. In some embodiments, the VLA-1 antagonist is administered to treat or prevent a secondary TBI.

In one embodiment, the subject has experienced a TBI within 48 hours, e.g., within 2, 3, 5, 8, 12, 20, or 30 hours of treatment. In another embodiment, the subject has experienced a TBI more than 48 hours before, but within the last three or two weeks, of treatment.

In one embodiment, the VLA-1 antagonist is administered in an amount sufficient to improve symptoms in one or more TBI assessment criterion, e.g., a criterion described herein, by at least 5, 10, 15, 20, 40, 50, 60, 70, or 80% or more.

In one embodiment, the VLA-1 antagonist is administered at a dosage of 0.025 mg/kg per day to 30 mg/kg per day, e.g., 0.1 to 5 mg/kg, e.g., 0.3 to 3 mg/kg. In one embodiment, the VLA-1 antagonist is administered at least twice within a 14 day period after a stroke, e.g., at least 3, 4, 5, 6, 7, 8, 9, 10, 11, 12, 13 or 14 times within a 14 day period after a stroke. The antagonist can be administered, for example, once daily, once every other day, twice a week, once a week, or once per day for 1 day, e.g., for 2, 3, 4, 5, 6, 7, 14 or 28 days. The VLA-1 antagonist can be administered intravenously or parenterally.

In one embodiment, the VLA-1 antagonist is administered in combination with a treatment for TBI. For example, the VLA-1 antagonist can be administered in conjunction with surgery and/or treatments for other injuries and infection. In a preferred embodiment, the VLA-1 antagonist and the second agent are administered at the same time. In a preferred embodiment, the VLA-1 antagonist is administered first in time and the second agent is administered second in time. In a preferred embodiment, the second agent is administered first in time and the VLA-1 antagonist is administered second in time.

In one embodiment, the method also includes evaluating the subject for a TBI criterion described herein. In some embodiments, the evaluation is performed at least 1 hour, e.g., at least 2, 4, 6, 8, 12, 24, or 48 hours, or at least 1 week, 2 weeks, 4 weeks, 10 weeks, 13 weeks, 20 weeks or more, after the administration of the VLA-1 antagonist. The subject can be evaluated in one or more of the following periods: prior to beginning of treatment; during the treatment; or after one or more elements of the treatment have been administered. Evaluating can include evaluating the need for further treatment with the same VLA-1 antagonist or for additional treatment with additional agents. In a preferred embodiment, if a preselected outcome of the evaluation is obtained, an additional step is taken, e.g., the subject is administered another treatment or another evaluation or test is performed.

In one aspect, the disclosure features a VLA-1 antagonist for use in treating TBI, e.g., as described herein. The antagonist can be a VLA-1 antagonist described herein, e.g., a VLA-1 antibody described herein. In another aspect, the disclosure features the use of a VLA-1 antagonist for the manufacture of a medicament for treating TBI, e.g., as described herein. The antagonist can be a VLA-1 antagonist described herein, e.g., a VLA-1 antibody described herein.

In one aspect, the disclosure features a container that includes a VLA-1 antagonist, e.g., a VLA-1 antibody, and a label with instructions for use of the antagonist in treating TBI.

In another aspect, the disclosure features methods of treating a spinal cord injury (SCI) in a subject. The method includes administering to the subject a VLA-1 antagonist in an amount effective to treat SCI.

In one embodiment, the VLA-1 antagonist is an anti-VLA-1 antibody, or antigen-binding fragment thereof. The anti-VLA-1 antibody can be a monoclonal antibody, or an antigen-binding fragment thereof. The anti-VLA-1 antibody can be full-length (e.g., an IgG (e.g., an IgG1, IgG2, IgG3, IgG4), IgM, IgA (e.g., IgA1, IgA2), IgD, and IgE) or can include only an antigen-binding fragment (e.g., a Fab, $F(ab')_2$ or scFv fragment, or one or more CDRs). An antibody, or antigen-binding fragment thereof, can include two heavy chain immunoglobulins and two light chain immunoglobulins, or can be a single chain antibody. The antibody can, optionally, include a constant region chosen from a kappa, lambda, alpha, gamma, delta, epsilon or a mu constant region gene. In some embodiments, the anti-VLA-1 antibody includes a heavy and light chain constant region substantially from a human antibody, e.g., a human IgG1 constant region or a portion thereof. In some embodiments, the anti-VLA-1 antibody is a human antibody.

In other embodiments, the antibody, or antigen-binding fragment thereof, is a chimeric or humanized antibody. As discussed herein, the antibodies can be CDR-grafted, humanized, or more generally, antibodies having CDRs from a non-human antibody and a framework that is selected as less immunogenic in humans, e.g., less antigenic than the murine framework in which a murine CDR naturally occurs.

In a preferred embodiment, the anti-VLA-1 antibody is a non-naturally occurring antibody, e.g., a chimeric, CDR-grafted, or humanized antibody having at least heavy chain CDR3, and preferably all heavy chain CDRs, more preferably all three heavy chain CDRs and all three light chain CDRs from a nonhuman antibody, e.g., a nonhuman antibody described herein. In a preferred embodiment, the CDRs can differ from a CDR referred to herein by 1, 2 or 3 amino acid residues, e.g., heavy chain CDR3 can be from a source described herein but otherwise another CDR can vary as described herein.

Preferred anti-VLA-1 antibodies include, e.g., a humanized AQC2 antibody (e.g., produced by a hybridoma having ATCC Deposit No. PTA-3274), AJH10 (ATCC PTA-3580), hAQC2 (ATCC PTA-3275), haAQC2 (ATCC PTA-3274), hsAQC2 (ATCC PTA-3356), mAQC2 (ATCC PTA-3273) and monoclonal antibody 1B3 (ATCC HB-10536). In some embodiments, the anti-VLA-1 antibody can bind to the same epitope as AQC2, AJH10, hAQC2, haAQC2, hsAQC2, mAQC2 and/or 1B3. In some embodiments, the anti-VLA-1 antibody competes with AQC2, AJH10, hAQC2, haAQC2, hsAQC2, mAQC2 and/or 1B3 for binding to VLA-1.

In some embodiments, the anti-VLA-1 antibody binds to the al subunit of VLA-1, e.g., the α1-I domain of VLA-1.

In one embodiment, the VLA-1 antagonist is a polypeptide, e.g., laminin or collagen I, III or IV, or a VLA-1 binding peptide of laminin or collagen I, III or IV described herein. In one embodiment, the VLA-1 antagonist is a VLA-1 peptide, e.g., a fragment of the al subunit, e.g., a fragment of the α1-1 domain containing the amino acid sequence VQRGGR (SEQ ID NO: 1) or a similar amino acid sequence with conservative amino acid substitutions. The laminin, collagen or VLA-1 peptides block VLA-1 function as tested by, e.g., its ability to inhibit K562-α1 dependent adhesion to collagen IV as described herein. In one embodiment, the VLA-1 antagonist is an inhibitor of the expression or translation of an VLA-1 nucleic acid, such as a double-stranded RNA (dsRNA) molecule, an antisense molecule, a ribozyme, a triple helix molecule, an aptamer or any combination thereof.

In one embodiment, the VLA-1 antagonist is a small molecule described herein (e.g., a chemical agent having a molecular weight of less than 2500 Da, preferably, less than 1500 Da), or a chemical, e.g., a small organic molecule.

In one embodiment, the VLA-1 antagonist can be administered in an amount and/or for a time sufficient to treat SCI, e.g., to cure, heal, alleviate, relieve, alter, remedy, ameliorate, improve or affect SCI, e.g., one or more symptoms of SCI described herein.

The subject is typically a mammal, e.g., human, dog, cat, monkey, rabbit, or agriculture mammal (e.g., horse, cow, pig, and so on). For example, the subject is a human, e.g., a human male or female. The subject can be at least 18, 25, 30, 45, 50, 55, 60, or 70 years old.

In some embodiments, the VLA-1 antagonist is administered to treat a primary SCI. In some embodiments, the VLA-1 antagonist is administered to treat or prevent a secondary SCI.

In one embodiment, the subject has experienced a SCI within 48 hours, e.g., within 2, 3, 5, 8, 12, 20, or 30 hours, of treatment. In another embodiment, the subject has experienced a SCI more than 48 hours before, but within the last three or two weeks, of treatment.

In one embodiment, the VLA-1 antagonist is administered in an amount sufficient to improve symptoms in one or more SCI assessment criterion, e.g., a criterion described herein, by at least 5, 10, 15, 20, 40, 50, 60, 70, or 80%, or more.

In one embodiment, the VLA-1 antagonist is administered at a dosage of 0.025 mg/kg per day to 30 mg/kg per day, e.g., 0.1 to 5 mg/kg, e.g., 0.3 to 3 mg/kg. In one embodiment, the VLA-1 antagonist is administered at least twice within a 14 day period after a stroke, e.g., at least 3, 4, 5, 6, 7, 8, 9, 10, 11, 12, 13 or 14 times within a 14 day period after a stroke. The antagonist can be administered, for example, once daily, once every other day, twice a week, once a week, or once per day for 1 day, e.g., for 2, 3, 4, 5, 6, 7, 14 or 28 days. The VLA-1 antagonist can be administered intravenously or parenterally.

In one embodiment, the VLA-1 antagonist is administered in combination with a second agent for treatment for SCI. The second agent can be, e.g., a corticosteroid or a glucocorticoid such as methylprednisolone. In a preferred embodiment, the VLA-1 antagonist and the second agent are administered at the same time. In a preferred embodiment, the VLA-1 antagonist is administered first in time and the second agent is administered second in time. In a preferred embodiment, the second agent is administered first in time and the VLA-1 antagonist is administered second in time.

In one embodiment, the method also includes evaluating the subject for a SCI criterion described herein. In some embodiments, the evaluation is performed at least 1 hour, e.g., at least 2, 4, 6, 8, 12, 24, or 48 hours, or at least 1 week, 2 weeks, 4 weeks, 10 weeks, 13 weeks, 20 weeks or more, after the administration of the VLA-1 antagonist. The subject can be evaluated in one or more of the following periods: prior to beginning of treatment; during the treatment; or after one or more elements of the treatment have been administered. Evaluating can include evaluating the need for further treatment with the same VLA-1 antagonist or for additional treatment with additional agents. In a preferred embodiment, if a preselected outcome of the evaluation is obtained, an additional step is taken, e.g., the subject is administered another treatment or another evaluation or test is performed.

In one aspect, the disclosure features a VLA-1 antagonist for use in treating SCI, e.g., as described herein. The antagonist can be a VLA-1 antagonist described herein, e.g., a VLA-1 antibody described herein. In another aspect, the disclosure features the use of a VLA-1 antagonist for the manufacture of a medicament for treating SCI, e.g., as described herein. The antagonist can be a VLA-1 antagonist described herein, e.g., a VLA-1 antibody described herein.

In one aspect, the disclosure features a container that includes a VLA-1 antagonist, e.g., a VLA-1 antibody, and a label with instructions for use of the antagonist in treating SCI.

As used herein, the term "treatment", "treat" or "treating" refers to administering a therapy in an amount, manner, and/or mode effective to improve a condition, symptom, or parameter associated with a disorder (e.g., stroke, TBI or SCI) or to reduce onset, progression, or exacerbation of the disorder (including secondary damage caused by the disorder, e.g., stroke, TBI or SCI), to either a statistically significant degree or to a degree detectable to one skilled in the art. Accordingly, treating can achieve therapeutic and/or prophylactic benefits. An effective amount, manner, or mode can vary depending on the subject and may be tailored to the subject. As used herein, "treatment" also encompasses the prophylactic treatment of subjects with an elevated risk for stroke, for example a subject who has experienced a transient ischemic attack. In a preferred embodiment, the VLA-1 antagonist is administered after the ischemic injury. In a preferred embodiment, the VLA-1 antagonist is administered after the subject has had a stroke.

As used herein, "an amount effective to treat", or a "therapeutically effective amount", refers to an amount of a VLA-1 antagonist that is effective, upon single or multiple dose administrations to a subject, to improve or prophylactically treat a condition, symptom, or parameter associated with a disorder or to reduce onset, progression, or exacerbation of the disorder, to either a statistically significant degree or to a degree detectable to one skilled in the art. For example, in the context of stroke, "an amount effective to treat" is an amount sufficient to reduce infarct size, e.g., by at least 5, 10, 15, 20, 40, 50, 60, 70, or 80% or more, in neuronal tissue in the brain, relative to the infarct size in an untreated subject. Alternatively, "an amount effective to treat" is an amount sufficient to improve symptoms in one or more stroke, TBI or SCI assessment criterion described herein by at least 5, 10, 15, 20, 40, 50, 60, 70, or 80% or more.

As used herein, "stroke" is a general term that refers to conditions caused by the occlusion or hemorrhage of one or more blood vessels supplying the brain, leading to cell death. "Ischemic stroke", as used herein, refers to stroke caused by an occlusion of one or more blood vessels supplying the brain. Types of ischemic stroke include, e.g., embolic stroke, cardioembolic stroke, thrombotic stroke, large vessel thrombosis, lacunar infarction, artery-artery stroke and cryptogenic stroke. "Hemorrhagic stroke", as used herein, refers to stroke caused by hemorrhage of one or more blood vessels supplying the brain. Types of hemorrhagic stroke include, e.g., subdural stroke, intraparenchymal stroke, epidural stroke and subarachnoid stroke.

As used herein, "traumatic brain injury" or "TBI" refers to damage to the brain caused by physical force or trauma. TBI can be primary of secondary. "Primary TBI" occurs immediately following the physical force or trauma and can result, e.g., in expanding hematoma, subarachnoid hemorrhage, cerebral edema, raised intracranial pressure, and cerebral hypoxia. "Secondary TBI" can occur over a period of hours to days following the physical force or trauma and can lead to severe secondary events (e.g., stroke). TBI is defined as "mild" when a patient scores between 13 and 15 on the Glasgow Coma Scale (GCS). Mild TBI can be associated with a loss of consciousness (LOC) for 5 minutes or less after the physical force or trauma and/or amnesia for a period of 10 minutes or less after the physical force or trauma. TBI is defined as "moderate to severe" when a patient scores less than 13 on the GCS.

As used herein, "spinal cord injury" or "SCI" refers to a traumatic injury sustained to the spinal cord and/or the area around it. The spinal cord may be compressed, severed or contused, leading to physical or physiological damage to the axons and affecting neuroelectrical impulse conduction along the length of the affected axons. Large populations of axons, including their associated cell bodies, may die, causing loss of communication between the brain and the peripheral nerves. SCI thus leads to sudden loss of complete or partial motor function, the extent of which depends on the location of the injury. Higher (cervical) SCI can result in total loss of motor function, quadriplegia, loss of respiratory control, and/or cardiovascular collapse. Lower (thoracic) SCI can result in paraplegia without involving arm or respiratory dysfunction.

All patents, patent applications, and references are hereby incorporated by reference in their entireties. In the case of conflict, the present application controls.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
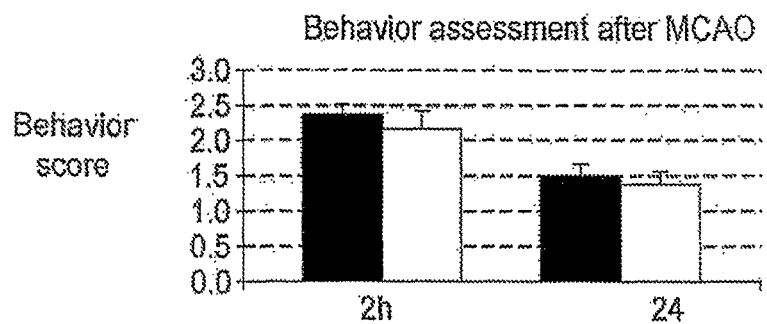
FIG. 1A is a graph of behavior assessment after MCAO.

The results presented herein show that a blocking VLA-1 antibody can reduce infarct size in vivo in a model of cerebral ischemia. The results demonstrate, among other things, that administration of a VLA-1 antagonist, e.g., a VLA-1 antibody, can reduce ischemic injury in the CNS, particularly traumatic ischemic injury. Accordingly, a VLA-1 antagonist, e.g., a VLA-1 antibody, can be administered to treat stroke, traumatic brain injury (TBI), and spinal cord injury (SCI), e.g., alone or in combination with another treatment, as well as other ischemic injuries.

VLA-1

Integrins are a superfamily of cell surface receptors that mediate cell-cell and cell-matrix adhesion. These proteins are known to provide anchorage as well as signals for cellular growth, migration and differentiation during development and tissue repair. They have been implicated in immune and inflammatory processes.

Integrins are heterodimeric proteins composed of two noncovalently linked polypeptide chains, α and β. The amino terminus of each chain forms a globular head that contributes to interchain linking and to ligand binding. The globular heads are connected to the transmembrane segments by stalks. The cytoplasmic tails are usually less than 50 amino acid residues long. Integrin subfamilies were originally defined on the basis of which β subunit was used to form the heterodimers. The β1-containing integrins are also called VLA molecules, referring to "very late activation" antigens. VLA-1 to VLA-6 refer to β1 subfamily members containing α1 to α6 (i.e., CD49a to CD49f), respectively. For general review, see *Cellular and Molecular Immunology*, eds. Abul K. Abbas et al., W.B. Saunders Company, Philadelphia, Pa., 2000.

Collagen (both types I and IV) and laminin are known ligands of α2β1 integrin (i.e., VLA-1). VLA-1 has been implicated in cell adhesion and migration on collagen (Keely et al., 1995, J. Cell Sci. 108: 595-607; and Gotwals et al., 1996, J. Clin. Invest. 97: 2469-2477); in promoting contraction and reorganization of collagen matrices, a critical component of wound healing (Gotwals et al., supra; and Chiro, 1991, Cell 67: 403-410); and in regulating the expression of genes involved in extracellular matrix remodeling (Riikonen et al., 1995, J. Biol. Chem. 270:1-5; and Langholz et al., 1995, J. Cell Biol. 131: 1903-1915).

VLA-1 Antagonists

A variety of agents can be used as VLA-1 antagonists to treat stroke. Such agents include antibodies to VLA-1 or to a part of VLA-1, e.g., to the α1 subunit of VLA-1. Some preferred agents include the anti-VLA-1 antibodies disclosed in U.S. Patent Applications 60/283,794, filed Apr. 14, 2001 and 60/303,689, filed Jul. 6, 2001, and disclosed in WO 02/083854. The disclosures of these applications are incorporated herein by reference in their entirety. Other agents include small molecules that block the interaction of VLA-1 to its ligand, e.g., collagen or laminin, or modulate integrin cell signaling to decrease a cellular activity or biochemical function associated with VLA-1. Agents useful in the methods disclosed herein also include those that reduce the expression of VLA-1, such as by gene therapy and antisense technology.

Anti-VLA-1 Antibodies

Exemplary VLA-1 antagonists include antibodies that bind to VLA-1. In one embodiment, the antibody inhibits the interaction between VLA-1 and a VLA-1 ligand (e.g., collagen), e.g., by physically blocking the interaction, decreasing the affinity of VLA-1 and/or a VLA-1 ligand for its counterpart, disrupting or destabilizing VLA-1 complexes, sequestering VLA-1, or targeting VLA-1 for degradation. In one embodiment, the antibody can bind to VLA-1 at one or more amino acid residues that participate in the VLA-1/ligand binding interface. Such amino acid residues can be identified, e.g., by alanine scanning. In another embodiment, the antibody can bind to residues that do not participate in the VLA-1/ligand binding. For example, the antibody can alter a conformation of VLA-1 and thereby reduce binding affinity, or the antibody may sterically hinder VLA-1/ligand binding. In one embodiment, the antibody can reduce activation of a VLA-1 mediated event or activity.

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$ fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A., et al. (1991) *Sequences of Proteins of Immunological Interest, Fifth Edition*, US Department of Health and Human Services, NIH Publication No. 91-3242; and Chothia, C. et al. (1987) *J. Mol. Biol.* 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulphide bond (see, e.g., A. F. Williams and A. N. Barclay (1988) *Ann. Rev Immunol.* 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with VLA-1.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (C1q) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Anti-VLA-1 antibodies can also be chimeric antibodies, e.g., generated by engineering a cognate (e.g., murine, rat or rabbit) antibody. For instance, a cognate antibody can be altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art. Preferred constant regions include, but are not limited to, those derived from IgG1 and IgG4.

Exemplary anti-VLA-1 antibodies useful in the methods described herein include, for example, monoclonal antibody AJH10 (ATCC PTA-3580; deposited on Aug. 2, 2001 with the American Type Culture Collection, 10801 University Boulevard, Manassas, Va. 20110-2209), hAQC2 (ATCC PTA-3275; deposited on Apr. 12, 2001), haAQC2 (ATCC PTA-3274; deposited on Apr. 12, 2001), hsAQC2 (ATCC PTA-3356; deposited on May 4, 2001) and mAQC2 (ATCC PTA-3273). All of these antibodies were deposited under the Budapest Treaty. Other anti-VLA-1 antibodies include, e.g., monoclonal antibody 1B3 (ATCC HB-10536) described in U.S. Pat. Nos. 5,391,481 and 5,788,966, and Ha31/8.

Antibody Generation

Antibodies that bind to VLA-1 can be generated by a variety of means, including immunization, e.g., using an animal, or in vitro methods such as phage display. All or part of VLA-1 can be used as an immunogen or as a target for selection. For example, VLA-1 or a fragment thereof, e.g., all or a part of an α1 subunit of VLA-1, e.g., an α1-I domain, can be used as an immunogen. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nat. Gen.* 7:13-21; US 2003-0070185; U.S. Pat. No. 5,789,650; and WO 96/34096.

Non-human antibodies to VLA-1 can also be produced, e.g., in a rodent. The non-human antibody can be humanized, e.g., as described in EP 239 400; U.S. Pat. Nos. 6,602,503; 5,693,761; and 6,407,213, deimmunized, or otherwise modified to make it effectively human.

EP 239 400 (Winter et al.) describes altering antibodies by substitution (within a given variable region) of their complementarity determining regions (CDRs) for one species with those from another. Typically, CDRs of a non-human (e.g., murine) antibody are substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody. Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; and 5,530,101; Tempest et al. (1991) *Biotechnology* 9:266-271 and U.S. Pat. No. 6,407, 213.

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" in the framework regions of the acceptor antibody in order to retain the antigen-binding activity of the cognate antibody. The general approach of making back mutations is known in the art. For instance, Queen et al. (supra), Co et al., Proc. Nat. Acad. Sci. USA88: 2869-2873 (1991), and WO 90/07861 (Protein Design Labs Inc.) describe an approach that involves two key steps. First, the human V framework regions are chosen by computer analysis for optimal protein sequence homology to the V region framework of the cognate murine antibody. Then, the tertiary structure of the murine V region is modeled by computer in order to visualize framework amino acid residues that are likely to interact with the murine CDRs, and these murine amino acid residues are then superimposed on the homologous human framework. Under this two-step approach, there are several criteria for designing humanized antibodies. The first criterion is to use as the human acceptor the framework from a particular human immunoglobulin that is usually homologous to the non-human donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, Biotechnology 9: 266-271 (1991). Under this approach, the V region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and V region framework residues can be readily modeled.

Fully human monoclonal antibodies that bind to VLA-1 can be produced, e.g., using in vitro-primed human splenocytes, as described by Boerner et al. (1991) *J. Immunol.* 147:86-95. They may also be prepared by repertoire cloning as described by Persson et al. (1991) *Proc. Nat. Acad. Sci. USA* 88:2432-2436 or by Huang and Stollar (1991) *J. Immunol. Methods* 141:227-236; also U.S. Pat. No. 5,798, 230. Large nonimmunized human phage display libraries may also be used to isolate high affinity antibodies that can be developed as human therapeutics using standard phage technology (see, e.g., Hoogenboom et al. (1998) *Immunotechnology* 4:1-20; Hoogenboom et al. (2000) *Immunol Today* 2:371-8; and US 2003-0232333). Other methods for producing fully human antibodies involve the use of non-human animals that have inactivated endogenous Ig loci and are transgenic for un-rearranged human antibody heavy chain and light chain genes. Such transgenic animals can be immunized with α1-I or a desired antigenic fragment thereof, and hybridomas are then made from B cells derived therefrom. These methods are described in, e.g., the various GenPharm/Medarex (Palo Alto, Calif.) publications/patents concerning transgenic mice containing human Ig miniloci (e.g., U.S. Pat. No. 5,789,650); the various Abgenix (Fremont, Calif.) publications/patents with respect to XENOMICE (e.g., U.S. Pat. Nos. 6,075,181; 6,150,584 and 6,162, 963; Green et al., Nature Genetics 7: 13-21 (1994); and Mendez et al., 15 (2): 146-56 (1997)); and the various Kirin (Japan) publications/patents concerning "transomic" mice (e.g., EP 843 961, and Tomizuka et al., Nature Genetics 16: 133-1443 (1997)).

Antibody and Protein Production

Antibodies and other proteins described herein can be produced in prokaryotic and eukaryotic cells. In one embodiment, the antibodies (e.g., scFv's) are expressed in a yeast cell such as *Pichia* (see, e.g., Powers et al. (2001) *J. Immunol. Methods* 251:123-35), *Hanseula*, or *Saccharomyces*.

Antibodies, particularly full length antibodies, e.g., IgG's, can be produced in mammalian cells. Exemplary mammalian host cells for recombinant expression include Chinese Hamster Ovary (CHO cells) (including dhfr-CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr⁻ host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/ amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies may also include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some proteins that include an Fc domain, the antibody/protein production system may be designed to synthesize antibodies or other proteins in which the Fc region is glycosylated. For example, the Fc domain of IgG molecules is glycosylated at asparagine 297 in the CH2 domain. The Fc domain can also include other eukaryotic post-translational modifications. In other cases, the protein is produced in a form that is not glycosylated.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody. The protein can be purified from the milk, or for some applications, used directly.

Other Moieties

The antibodies described herein may further comprise other moieties to effect the desired functions. For instance, the antibodies may include atoxin moiety (e.g., tetanus toxoid or ricin) or a radionuclide (e.g., $^{111}$In or $^{90}$Y) for killing of cells targeted by the antibodies (see, e.g., U.S. Pat. No. 6,307,026). The antibodies may comprise a moiety (e.g., biotin, fluorescent moieties, radioactive moieties, histidine tags, etc.) for easy isolation or detection. The antibodies may also comprise a moiety that can prolong their serum half life, for example, a polyethylene glycol (PEG) moiety.

Polypeptide Antagonists

In addition to antibodies, VLA-1 antagonists useful in the methods described herein include polypeptides that inhibit the function of VLA-1, e.g., by blocking the interaction between VLA-1 and its physiological ligands such as collagen, e.g., collagen I, III, or IV, or laminin, or by modulating VLA-1-dependent cell signaling.

A VLA-1 antagonist is an agent that has one or more of the following properties: (1) it coats, or binds to, a VLA-1 antigen on the surface of a VLA-1 bearing cell with sufficient specificity to inhibit a VLA-1/VLA-1-ligand interaction, e.g., the VLA-1/collagen interaction; (2) it coats, or binds to, a VLA-1 antigen on the surface of a VLA-1 bearing cell with sufficient specificity to modify, and preferably to inhibit, transduction of a VLA-1-mediated signal, e.g., VLA-1/collagen-mediated signaling; (3) it coats, or binds to, a VLA-1-ligand, e.g., collagen (e.g., collagen I, III or IV) or laminin, with sufficient specificity to inhibit the VLA-1 NLA-1-ligand interaction; (4) it coats, or binds to, a VLA-1-ligand, e.g., collagen (e.g., collagen I, III or IV) or laminin, with sufficient specificity to modify, and preferably to inhibit, transduction of VLA-1-ligand mediated VLA-1 signaling, e.g., collagen-mediated VLA-1 signaling. In preferred embodiments the VLA-1 antagonist has one or both of properties 1 and 2. In other preferred embodiments the VLA-1 antagonist has one or both of properties 3 and 4.

For purposes of the methods described herein, any agent capable of binding to VLA-1 antigens on the surface of VLA-1 bearing cells and that effectively blocks or coats VLA-1 antigens, is considered to be an equivalent of the monoclonal antibody used in the examples herein.

As discussed herein, the VLA-1 antagonists used in methods described herein are not limited to antibodies or antibody derivatives, but may be other molecules, e.g., soluble forms of other proteins that bind VLA-1, e.g., the natural binding proteins for VLA-1. These antagonists include collagen I, III, or IV; VLA-1 binding peptides of collagen I, III or IV; laminin; and VLA-1 binding peptides of laminin (see, e.g., Pfaff et al, Eur. J. Biochem. 225:975-84, 1994; Colognato-Pyke et al, J. Biol. Chem. 270: 9398-9406, 1995; and Colognato et al., J. Biol. Chem. 272: 29330-29336, 1997). For example, VLA-1 binding peptides of collagen I, III or IV can contain the amino acid sequence GFOGER (SEQ ID NO:2) (see, e.g. Knight et al., J. Biol. Chem. 275:35-40, 2000), GFOGER (SEQ ID NO:3) (see, e.g., Kim et al., J. Biol. Chem. 280:32512-32520, 2005), or a similar conservatively substituted amino acid sequence. Other antagonists include VLA-1 peptides, such as a peptide containing the amino acid sequence VQRGGR (SEQ ID NO: 1) or a similar conservatively substituted amino acid sequence, and peptide mimetics, such as those described in WO 01/96365; U.S. Pat. Nos. 6,326,403 and 6,001,961. These antagonists can act by competing with the cell-surface binding protein for VLA-1 or by otherwise altering VLA-1 function.

Small Molecule Antagonists

In addition to antibodies, VLA-1 antagonists useful in the methods described herein include any non-antibody compounds that inhibit the function of VLA-1, e.g., by blocking the interaction between VLA-1 and its physiological ligands such as collagen, or by modulating VLA-1-dependent cell signaling. Examples of these compounds are small molecule compounds, e.g., those described in Weitz-Schmidt et al., Nat. Med. 7:687-692, 2001). These compounds can be identified using, e.g., combinatorial small molecule libraries, combinatorial antibody libraries, rational drug designs, and traditional organic synthesis followed by screening for antagonism using any method known in the art.

In one example, recombinantly expressed VLA-1 or functional fragments thereof can be used to screen libraries of natural, semisynthetic or synthetic compounds. Particularly useful types of libraries include combinatorial small organic molecule libraries, phage display libraries, and combinatorial peptide libraries.

Methods of determining whether components of the library bind to a particular polypeptide are well known in the art. In general, the polypeptide target is attached to solid support surface by non-specific or specific binding. Specific binding can be accomplished using an antibody which recognizes the protein that is bound to a solid support, such as a plate or column. Alternatively, specific binding may be through an epitope tag, such as GST binding to a glutathione-coated solid support, or IgG fusion protein binding to a Protein A solid support.

Alternatively, the recombinantly expressed VLA-1 or parts thereof may be expressed on the surface of phage, such as M13. A library in mobile phase is incubated under conditions to promote specific binding between the target and a compound. Compounds that bind to the target can then be identified. Alternately, the library is attached to a solid support and the polypeptide target is in the mobile phase.

Binding between a compound and the VLA-1 target can be determined by a number of methods. The binding can be identified by such techniques as competitive ELISAs or RIAs, for example, wherein the binding of a compound to a target will reduce binding of an antibody to the same target. These methods are well-known in the art. Another method is to use BiaCORE to measure interactions between a target and a compound using methods provided by the manufacturer. A preferred method is automated high throughput screening, see, e.g., Burbaum et al., Curr OpinChem. Biol. 1: 72-8 (1997), and Schullek et al., Anal Biochem. 246: 20-9 (1997).

Once a candidate compound that binds to a target is identified, one can determine whether the compound inhibits the activity of the target. For instance, the candidate compound can be used to screen for its ability to inhibit K562-α1 dependent adhesion to collagen IV. See, e.g., U.S. Application 60/303,689 and WO 02/083854. In another example, the candidate compound is used to compete for binding of an anti-VLA-1 antibody to (1) a VLA-1-expressing cell, or (2) a molecule containing the α1β1 integrin or a fragment thereof, e.g., the α1-I domain.

Another method to identify VLA-1 antagonists is to use the structure of recombinantly expressed VLA-1 for rational drug design. See, e.g., WO 01/73444.

Nucleic Acid Antagonists

In certain implementations, nucleic acid antagonists are used to decrease expression of an endogenous gene encoding VLA-1. In one embodiment, the nucleic acid antagonist is an siRNA that targets mRNA encoding VLA-1. Other types of blocking nucleic acids can also be used, e.g., a dsRNA, a ribozyme, a triple-helix former, an aptamer, or an antisense nucleic acid.

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). See, e.g., Clemens et al. (2000)*Proc. Natl. Acad. Sci. USA* 97:6499-6503; Billy et al. (2001) *Proc. Natl. Sci. USA* 98:14428-14433; Elbashir et al. (2001) *Nature.* 411:494-8; Yang et al. (2002) *Proc. Natl. Acad. Sci. USA* 99:9942-9947, U.S. 20030166282, 20030143204, 20040038278, and 20030224432.

Anti-sense agents can include, for example, from about 8 to about 80 nucleobases (i.e. from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding VLA-1) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding VLA-1. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include $N^4$—$(C_1$-$C_{12})$ alkylaminocytosines and $N^4,N^4$—$(C_1$-$C_{12})$ dialkylaminocytosines. Modified nucleobases may also include 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—$(C_1$-$C_{12})$ alkylaminopurines and $N^6,N^6$—$(C_1$-$C_{12})$ dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine. Derivatives of any of the aforementioned modified nucleobases are also appropriate. Substituents of any of the preceding compounds may include $C_1$-$C_{30}$ alkyl, $C_2$-$C_{30}$ alkenyl, $C_2$-$C_{30}$ alkynyl, aryl, aralkyl, heteroaryl, halo, amino, amido, nitro, thio, sulfonyl, carboxyl, alkoxy, alkylcarbonyl, alkoxycarbonyl, and the like.

Descriptions of other types of nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

The nucleic acids described herein, e.g., an anti-sense nucleic acid described herein, can be incorporated into a gene construct to be used as a part of a gene therapy protocol to deliver nucleic acids that can be used to express and produce agents, e.g., anti-sense nucleic acids within cells. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis et al. (1985) *Science* 230:1395-1398; Danos and Mulligan (1988) *Proc. Natl. Acad. Sci. USA* 85:6460-6464; Wilson et al. (1988) *Proc. Natl. Acad. Sci. USA* 85:3014-3018; Armentano et al. (1990) *Proc. Natl. Acad. Sci. USA* 87:6141-6145; Huber et al. (1991) *Proc. Natl. Acad. Sci. USA* 88:8039-8043; Ferry et al. (1991) *Proc. Natl. Acad. Sci. USA* 88:8377-8381; Chowdhury et al. (1991) *Science* 254:1802-1805; van Beusechem et al. (1992) *Proc. Natl. Acad. Sci. USA* 89:7640-7644; Kay et al. (1992) *Human Gene Therapy* 3:641-647; Dai et al. (1992) *Proc. Natl. Acad. Sci. USA* 89:10892-10895; Hwu et al. (1993) *J. Immunol.* 150:4104-4115; U.S. Pat. Nos. 4,868,116 and 4,980,286; PCT Application WO 89/07136; PCT Application WO 89/02468; PCT Application WO 89/05345; and PCT Application WO 92/07573).

Another viral gene delivery system utilizes adenovirus-derived vectors. See, for example, Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are known to those skilled in the art.

Yet another viral vector system useful for delivery of the subject gene is the adeno-associated virus (AAV). See, for example, Flotte et al. (1992) *Am. J. Respir. Cell. Mol. Biol.* 7:349-356; Samulski et al. (1989) *J. Virol.* 63:3822-3828; and McLaughlin et al. (1989) *J. Virol.* 62:1963-1973.

Aptamers

Aptamers are short oligonucleotide sequences that can be used to recognize and specifically bind almost any molecule, including cell surface proteins. The systematic evolution of ligands by exponential enrichment (SELEX) process is powerful and can be used to readily identify such aptamers. Aptamers can be made for a wide range of proteins of importance for therapy and diagnostics, such as growth factors and cell surface antigens. These oligonucleotides bind their targets with similar affinities and specificities as antibodies do (see Ulrich (2006) Handb Exp Pharmacol. 173:305-26). Macugen® is an approved aptamer therapeutic which is also the first anti-angiogenic agent approved for a common eye disorder.

Artificial Transcription Factors

Artificial transcription factors can also be used to regulate expression of VLA-1. The artificial transcription factor can be designed or selected from a library, e.g., for ability to bind to a sequence in an endogenous gene encoding VLA-1, e.g., in a regulatory region, e.g., the promoter. For example, the artificial transcription factor can be prepared by selection in vitro (e.g., using phage display, U.S. Pat. No. 6,534,261) or in vivo, or by design based on a recognition code (see, e.g., WO 00/42219 and U.S. Pat. No. 6,511,808). See, e.g., Rebar et al. (1996) *Methods Enzymol* 267:129; Greisman and Pabo (1997) *Science* 275:657; Isalan et al. (2001) *Nat. Biotechnol* 19:656; and Wu et al. (1995) *Proc. Natl. Acad. Sci. USA* 92:344 for, among other things, methods for creating libraries of varied zinc finger domains.

Optionally, an artificial transcription factor can be fused to a transcriptional regulatory domain, e.g., an activation domain to activate transcription or a repression domain to repress transcription. In particular, repression domains can be used to decrease expression of endogenous genes encoding VLA-1. The artificial transcription factor can itself be encoded by a heterologous nucleic acid that is delivered to a cell or the protein itself can be delivered to a cell (see, e.g., U.S. Pat. No. 6,534,261). The heterologous nucleic acid that includes a sequence encoding the artificial transcription factor can be operably linked to an inducible promoter, e.g., to enable fine control of the level of the artificial transcription factor in the cell, e.g., a neuronal or glial cells, e.g., at or near a site of stroke injury or another injury described herein.

Ischemic Injuries

Ischemia refers to a reduction or abolition of blood supply to a tissue. The methods described herein can be used to treat injuries associated with ischemia, or "ischemic injuries". Ischemic injuries can include injuries to, e.g., the kidney, liver, lungs, pancreas, skeletal muscle, intestines, heart and brain. Ischemic injuries can be associated with or caused by, e.g., acute myocardial infarction, elective angioplasty, coronary artery bypass graft, surgery involving cardiac bypass or organ or tissue transplantation (e.g., cardiac transplantation), tissue rejection after transplantation, graft versus host disease, stroke, head trauma, drowning, sepsis, cardiac arrest, shock, atherosclerosis, hypertension, cocaine-induced heart disease, smoking-induced heart disease, heart failure, pulmonary hypertension, hemorrhage, capillary leak syndrome (such as child and adult respiratory distress syndrome), multi-organ system failure, a state of low colloid oncotic pressure (such as starvation, anorexia nervosa, or hepatic failure with decreased production of serum proteins), anaphylaxis, hypothermia, cold injury (e.g., due to hypothermic perfusion or frostbite) hepatorenal syndrome, delirium tremens, a crush injury, mesenteric insufficiency, peripheral vascular disease, claudication, burn, electrocution, excessive drug-induced vasodilation, excessive drug-induced vasoconstriction, radiation exposure (e.g., during fluoroscopy or radiographic imaging), or exposure to high energy, e.g., exposure to laser light. Excessive drug-induced vasodilation can be caused by, for instance, nitroprusside, hydralazone, dyazoxide, a calcium channel blocker, or a general anesthetic. Excessive drug-induced vasoconstriction can be caused by, for instance, neosynephrine, isoproterenol, dopamine, dobutamine, or cocaine.

Ischemia-Reperfusion Injury

"Ischemia-reperfusion injury" refers to an injury that results from the re-establishment (reperfusion) of the flow of blood to a region of the body following a temporary halt in the flow. For example, ischemia-reperfusion injury can occur during certain surgical procedures, such as repair of aortic aneurysms and organ transplantation. Clinically, ischemia-reperfusion injury can be manifested by complications such as, e.g., pulmonary dysfunction, including adult respiratory distress syndrome, renal dysfunction, consumptive coagulopathies including thrombocytopenia, fibrin deposition into the microvasculature and disseminated intravascular coagulopathy, transient and permanent spinal cord injury, cardiac arrhythmias and acute ischemic events, hepatic dysfunction including acute hepatocellular damage and necrosis, gastrointestinal dysfunction including hemorrhage and/or infarction and multisystem organ dysfunction (MSOD) or acute systemic inflammatory distress syndromes (SIRS). The injury may occur in the parts of the body to which the blood supply was interrupted, or it can occur in parts fully supplied with blood during the period of ischemia.

Stroke

Stroke is a general term for acute brain damage resulting from disease or injury of blood vessels. Stroke can be classified into at least two main categories: hemorrhagic stroke (resulting from leakage of blood outside of the normal blood vessels) and ischemic stroke (cerebral ischemia due to lack of blood supply). Some events that can cause ischemic stroke include thrombosis, embolism, and systemic hypoperfusion (with resultant ischemia and hypoxia).

Stroke generally causes neuronal death and injury in the brain by oxygen deprivation and secondary events. The area of the brain that dies as a result of the lack of blood supply or other damage is called an infarct. In some cases, the treatments described herein can be used to reduce or minimize the size of an infarct, e.g., by reducing secondary events that cause neuronal death or injury.

Obstruction of a cerebral artery resulting from a thrombus which has built up on the wall of a brain artery is generally called cerebral thrombosis. In cerebral embolism, the occlusive material blocking the cerebral artery arises downstream in the circulation (e.g., an embolus is carried to the cerebral artery from the heart). Because it is difficult to discern whether a stroke is caused by thrombosis or embolism, the term thromboembolism is used to cover both these types of stroke. Systemic hypoperfusion may arise as a consequence of decreased blood levels, reduced hematocrit, low blood pressure or inability of the heart to pump blood adequately.

Thrombolytic agents, such as tissue plasminogen activator (t-PA), have been used in the treatment of thromboembolic stroke. These molecules function by lysing the thrombus causing the ischemia. Such drugs are believed to be most useful if administered as soon as possible after acute stroke (preferably within 3 hours) in order to at least partially restore cerebral blood flow in the ischemic region and to sustain neuronal viability. A VLA-1 antagonist can be used, instead of or in combination with, such thrombolytic agents, to achieve a therapeutic benefit in a subject who has experienced a thromboembolic stroke.

Because thrombolytic agents exacerbate bleeding, their use in hemorrhagic stroke is contra-indicated. However, a VLA-1 antagonist can be used to provide therapeutic benefit in cases of hemorrhagic stroke.

Further, a VLA-1 antagonist can be administered as a prophylactic stroke therapy, or as a component thereof, e.g., to a subject who has experienced a TIA or is exhibiting symptoms of TIA. When symptoms of stroke last fewer than 24 hours and the subject recovers completely, the subject is said to have undergone a transient ischemic attack (TIA). The symptoms of TIA include a temporary impairment of speech, vision, sensation, or movement. Because a TIA is often thought to be a prelude to full-scale stroke, subjects having suffered a TIA are candidates for prophylactic stroke therapy, e.g., with a VLA-1 antagonist alone or in combination with another agent, e.g., an anticoagulation agent (e.g., coumarin and heparin) or an antiplatelet agent (such as aspirin and ticlopidine).

Other Stroke Treatments

A stroke treatment can involve the use of one or more VLA-1 antagonists that can be used in combination with one or more stroke treatments. The treatments can be administered at the same time, but also at separate times, e.g., at separate times that are within a specified interval, e.g., within the same 48, 24, 12, 6, 2, or 1 hour. Furthermore, the treatments can be using distinct modes of administration.

Treatments that can be administered in combination with a VLA-1 antagonist include: a thrombolytic agent (e.g., streptokinase, acylated plasminogen-streptokinase activator complex (APSAC), urokinase, single-chain urokinase-plasminogen activator (scu-PA), anti-inflammatory agents, thrombin-like enzymes from snake venoms such as ancrod, thrombin inhibitors, tissue plasminogen activator (t-PA) and biologically active variants of each of the above); an anticoagulant (e.g., warfarin or heparin); antiplatelet drug (e.g., aspirin); a glycoprotein IIb/IIIa inhibitor; a glycosaminoglycan; coumarin; GCSF; melatonin; a caspase inhibitor; an anti-oxidants (e.g., NXY-059, see Lees et al., (2006) *N. Engl. J. Med* 354, 588-600), a neuroprotectant (e.g., an NMDA receptor antagonist and a cannabinoid antagonist), an anti-CD18 antibody; an anti-CD11a antibody; an anti-ICAM-1 antibody; an anti-VLA-4 antibody, an anti-TWEAK antibody, an anti-TWEAK-R antibody, carotid endarterectomy; angioplasty; insertion of a stent; and an alternative medicine (e.g., acupuncture, traditional Chinese medicine, meditation, massage, hyperbaric oxygen treatment, or conductive pedagogy).

Particular examples of combination treatments include administering a VLA-1 antagonist to a subject who has experienced a stroke shortly after the onset of stroke symptoms and at the same time as another treatment, such as t-PA. The following day, the subject can further commence daily treatments with an anti-platelet drug to protect against a future stroke and later receive additional doses of the VLA-1 antagonist, to maintain bioavailability of the VLA-1 antagonist. As another example, a subject who has experienced a TIA may begin VLA-1 antagonist treatment immediately after diagnosis of the TIA at a dose that provides a biological effect for at least a week, and then begin anti-platelet therapy the following day.

Stroke Risk Factors

Risk factors for stroke can be used to identify a subject who can be provided with a prophylactic dose of a VLA-1 antagonist or who should be monitored for further signs that treatment with a VLA-1 antagonist is required. In some cases, the subject is treated if the subject has two, three, or four or more of risk factors, e.g., factors listed below.

High Blood Pressure:

High blood pressure (140/90 mm Hg or higher) is a highly significant risk factor for stroke.

Tobacco Use:

Cigarette smoking is a major, preventable risk factor for stroke. The nicotine and carbon monoxide in tobacco smoke reduce the amount of oxygen in the blood. They also damage the walls of blood vessels, making clots more likely to form. Using some kinds of birth control pills combined with smoking cigarettes greatly increases stroke risk.

Diabetes Mellitus:

Diabetes is defined as a fasting plasma glucose (blood sugar) of 126 mg/dL or more measured on two occasions. While diabetes is treatable, having it still increases a person's risk of stroke. Many people with diabetes also have high blood pressure, high blood cholesterol and are overweight. These additional factors further increase risk of stroke.

Carotid or Other Artery Disease:

The carotid arteries in the neck supply blood to your brain. A carotid artery narrowed by fatty deposits from atherosclerosis (plaque buildups in artery walls) may become blocked by a blood clot. Carotid artery disease is also called carotid artery stenosis.

Peripheral Artery Disease:

Subjects with peripheral artery disease have a higher risk of carotid artery disease, which raises their risk of stroke. Peripheral artery disease is the narrowing of blood vessels carrying blood to leg and arm muscles. It is caused by fatty buildups of plaque in artery walls.

Atrial fibrillation raises the risk for stroke. The upper chambers of the heart quiver instead of beating effectively, which can let the blood pool and clot. If a clot breaks off, enters the bloodstream and lodges in an artery leading to the brain, a stroke results.

Other Heart Disease:

Subjects with coronary heart disease or heart failure have a higher risk of stroke than those with hearts that work normally. Dilated cardiomyopathy (an enlarged heart), heart valve disease and some types of congenital heart defects also raise the risk of stroke.

Transient Ischemic Attacks (TIAs):

TIAs are "warning strokes" that produce stroke-like symptoms but no lasting damage. Recognizing and treating TIAs can reduce the risk of a major stroke.

Certain Blood Disorders:

A high red blood cell count thickens the blood and makes clots more likely. This raises the risk of stroke. Sickle cell disease (also called sickle cell anemia) is a genetic disorder that mainly affects African Americans. "Sickled" red blood cells are less able to carry oxygen to the body's tissues and organs and tend to stick to blood vessel walls, which can block arteries to the brain and cause a stroke.

High Blood Cholesterol:

A high level of total cholesterol in the blood (240 mg/dL or higher) is a major risk factor for heart disease, which raises the risk of stroke. High levels of LDL cholesterol (greater than 100 mg/dL) and triglycerides (blood fats, 150 mg/dL or higher) increase the risk of stroke in people with previous coronary heart disease, ischemic stroke or transient ischemic attack (TIA). Low levels (less than 40 mg/dL) of HDL cholesterol also may raise stroke risk.

Physical Inactivity and Obesity:

Being inactive, obese, or both can increase the risk of high blood pressure, high blood cholesterol, diabetes, heart disease, and stroke.

Excessive Substance Abuse:

Drinking excessive amounts of alcohol and intravenous drug use can also increase risk for stroke.

Increasing Age:

Although subjects of all ages, including children, have strokes, the older the subject is, the greater the risk for stroke. For example, risk can be much greater over the age of 55, 60, 70, 80, or 85.

Sex (Gender):

Stroke is more common in men than in women. In most age groups, more men than women will have a stroke in a given year. However, women account for more than half of all stroke deaths. Women who are pregnant have a higher stroke risk.

Heredity (Family History):

The stroke risk is greater if a parent, grandparent, sister, or brother has had a stroke. Similarly, certain ethnic backgrounds can lead to an increased risk for stroke.

Prior Stroke or Heart Attack:

A subject who has had a stroke or a heart attack is at much higher risk of subsequently having a stroke.

Stroke Assessment Criteria

The ability of a VLA-1 antagonist to treat a subject having or at risk for stroke can be evaluated, subjectively or objectively, e.g., using a variety of criteria. A number of assessment tools are available to provide the evaluation.

Exemplary prehospital stroke assessment tools include the Cincinnati Stroke Scale and the Los Angeles Prehospital Stroke Screen (LAPSS). Acute assessment scales include, e.g., the Canadian Neurological Scale (CNS), the Glasgow Coma Scale (GCS), the Hempispheric Stroke Scale, the Hunt & Hess Scale, the Mathew Stroke Scale, the Mini-Mental State Examination (MMSE), the NIH Stroke Scale (NIHSS), the Orgogozo Stroke Scale, the Oxfordshire Community Stroke Project Classification (Bamford), and the Scandinavian Stroke Scale. Functional assessment scales include the Berg Balance Scale, the Modified Rankin Scale, the Stroke Impact Scale (SIS), and the Stroke Specific Quality of Life Measure (SS-QOL). Outcome assessment tools include the American Heart Association Stroke Outcome Classification (AHA SOC), the Barthel Index, the Functional Independence Measurement (FIM™), the Glasgow Outcome Scale (GOS), and the 36-item and 12-item short-form health outcomes surveys SF-36® and SF-12®, respectively. Other diagnostic and screening tests include the Action Research Arm Test, the Blessed-Dementia Scale, the Blessed-Dementia Information-Memory-Concentration Test, the DSM-IV criteria for the diagnosis of vascular dementia, the Hachinkski Ischaemia Score, the Hamilton Rating Scale for Depression, the NINDS-AIREN criteria for the diagnosis of vascular dementia, the Orpington Prognostic Score, the Short Orientation-Memory-Concentration Test, the Thrombosis In Myocardial Infarction grading scheme, MRI imaging (e.g., diffusion and perfusion imaging techniques (Henninger et al., Stroke 37:1283-1287, 2006), diffusion-weighted (DWI) MRI techniques, and flow-sensitive imaging, e.g., fluid-attenuated inversion recovery (FLAIR)), functional and spectroscopical imaging (Koroshetz, Ann. Neurol. 39:283-284, 1996), and PET (Heiss et al., Cerebrovasc. Brain Metab. Rev. 5:235-263, 1993).

An evaluation can be performed before and/or after the administration of a VLA-1 antagonist.

Traumatic Brain Injury

A VLA-1 antagonist described herein can be used to treat traumatic brain injury. Damage to the brain by a physical force is broadly termed traumatic brain injury (TBI). The resulting effect of TBI causes alteration of normal brain processes attributable to changes in brain structure and/or function. There are two basic types of brain injury, open head injury and closed head injury. In an open head injury, an object, such as a bullet, penetrates the skull and damages the brain tissue. Closed head injury is usually caused by a rapid movement of the head during which the brain is whipped back and forth, bouncing off the inside of the skull. Closed head injuries are the most common of the two, which often result from accidents involving motor vehicles or falls. In a closed head injury, brute force or forceful shaking injures the brain. The stress of this rapid movement pulls apart and stretches nerve fibers or axons, breaking connections between different parts of the brain. In most cases, a resulting blood clot, or hematoma, may push on the brain or around it, raising the pressure inside the head. Both open and closed head injuries can cause severe damage to the brain, resulting in the need for immediate medical attention.

Depending on the type of force that hits the head, varying injuries such as any of the following can result: jarring of the brain within the skull, concussion, skull fracture, contusion, subdural hematoma, or diffuse axonal injury. Though each person's experience is different, there are common problems that many people with TBI face. Possibilities documented include difficulty in concentrating, ineffective problem solving, short and long-term memory problems, and impaired motor or sensory skills; to the point of an inability to perform daily living skills independently such as eating, dressing or bathing. The most widely accepted concept of brain injury divides the process into primary and secondary events. Primary brain injury is considered to be more or less complete at the time of impact, while secondary injury evolves over a period of hours to days following trauma.

Primary injuries are those commonly associated with emergency situations such as auto accidents, or anything causing temporary loss of consciousness or fracturing of the skull. Contusions, or bruise-like injuries, often occur under the location of a particular impact. The shifting and rotating of the brain inside the skull after a closed brain injury results in shearing injury to the brain's long connecting nerve fibers or axons, which is referred to as diffuse axonal injury. Lacerations are defined as the tearing of frontal and temporal lobes or blood vessels caused by the brain rotating across ridges inside the skull. Hematomas, or blood clots, result when small vessels are broken by the injury. They can occur between the skull and the brain (epidural or subdural hematoma), or inside the substance of the brain itself (intracerebral hematoma). In either case, if they are sufficiently large they will compress or shift the brain, damaging sensitive structures within the brain stem. They can also raise the pressure inside the skull and eventually shut off the blood supply to the brain.

Delayed secondary injury at the cellular level has come to be recognized as a major contributor to the ultimate tissue loss that occurs after brain injury. A cascade of physiologic, vascular, and biochemical events is set in motion in injured tissue. This process involves a multitude of systems, including possible changes in neuropeptides, electrolytes such as calcium and magnesium, excitatory amino acids, arachidonic acid metabolites such as the prostaglandins and leukotrienes, and the formation of oxygen free radicals. This secondary tissue damage is at the root of most of the severe, long-term adverse effects a person with brain injury may experience. Procedures that minimize this damage can be the difference between recovery to a normal or near-normal condition, or permanent disability.

Diffuse blood vessel damage has been increasingly implicated as a major component of brain injury. The vascular response seems to be biphasic. Depending on the severity of the trauma, early changes include an initial rise in blood pressure, an early loss of the automatic regulation of cerebral blood vessels, and a transient breakdown of the blood-brain barrier (BBB). Vascular changes peak at approximately six hours post-injury but can persist for as long as six days. The clinical significance of these blood vessels changes is still unclear, but may relate to delayed brain swelling that is often seen, especially in younger people.

The process by which brain contusions produce brain necrosis is equally complex and is also prolonged over a period of hours. Toxic processes include the release of oxygen free radicals, damage to cell membranes, opening of ion channels to an influx of calcium, release of cytokines, and metabolism of free fatty acids into highly reactive substances that may cause vascular spasm and ischemia. Free radicals are formed at some point in almost every mechanism of secondary injury. The primary target of the free radicals are the fatty acids of the cell membrane. A process known as lipid peroxidation damages neuronal, glial, and vascular cell membranes in a geometrically progressing fashion. If unchecked, lipid peroxidation spreads over the surface of the cell membrane and eventually leads to cell death. Thus, free radicals damage endothelial cells, disrupt the blood-brain barrier (BBB), and directly injure brain cells, causing edema and structural changes in neurons and glia. Disruption of the BBB is responsible for brain edema and exposure of brain cells to damaging blood-borne products.

Secondary systemic insults (outside the brain) may consequently lead to further damage to the brain. This is extremely common after brain injuries of all grades of severity, particularly if they are associated with multiple injuries. Thus, people with brain injury may experience combinations of low blood oxygen, blood pressure, heart and lung changes, fever, blood coagulation disorders, and other adverse changes at recurrent intervals in the days following brain injury. These occur at a time when the normal regulatory mechanism, by which the cerebralvascular vessels can relax to maintain an adequate supply of oxygen and blood during such adverse events, is impaired as a result of the original trauma.

The protocols for immediate assessment are limited in their efficiency and reliability and are often invasive. Computer-assisted tomographic (CT) scanning is currently accepted as the standard diagnostic procedure for evaluating TBI, as it can identify many abnormalities associated with primary brain injury, is widely available, and can be performed at a relatively low cost (Marik et al. Chest 122:688-711 2002; McAllister et al. Journal of Clinical and Experimental Neuropsychology 23:775-791 2001). However, the use of CT scanning in the diagnosis and management of patients presenting to emergency departments with TBI can vary among institutions, and CT scan results themselves may be poor predictors of neuropsychiatric outcome in TBI subjects, especially in the case of mild TBI injury (McCullagh et al. Brain Injury 15:489-497 2001).

Immediate treatment for TBI typically involves surgery to control bleeding in and around the brain, monitoring and controlling intracranial pressure, insuring adequate blood flow to the brain, and treating the body for other injuries and infection. Those with mild brain injuries often experience subtle symptoms and may defer treatment for days or even weeks. Once a patient chooses to seek medical attention, observation, neurological testing, magnetic resonance imaging (MRI), positron emission tomography (PET) scan, single-photon emission CT (SPECT) scan, monitoring the level of a neurotransmitter in spinal fluid, computed tomography (CT) scans, and X-rays may be used to determine the extent of the patient's injury. The type and severity of the injury determine further care.

A VLA-1 antagonist can be used, alone or in combination with another treatment, to achieve a therapeutic benefit in a subject who has experienced a TBI. Further, a VLA-1 antagonist can be administered as a prophylactic TBI therapy, or as a component thereof, e.g., to a subject who has experienced a TBI or is exhibiting symptoms of a TBI. For example, a VLA-1 antagonist can be used to treat a primary injury, a secondary injury, or both. Alternatively, a VLA-1 antagonist can be used to treat a primary injury and as a prophylactic therapy for a secondary injury. An evaluation can be performed before and/or after the administration of a VLA-1 antagonist.

Spinal Cord Injury

A VLA-1 antagonist described herein can be used to treat spinal cord injury. Spinal cord injury (SCI) is an insult to the spinal cord resulting in a change, either temporary or permanent, in its normal motor, sensory, or autonomic function. Both clinical and experimental studies evidence that the spinal cord suffers from primary and secondary damage after acute SCI. Primary SCI arises from mechanical disruption, transection, extradural pathology, or distraction of neural elements. This injury usually occurs with fracture and/or dislocation of the spine. However, primary SCI may occur in the absence of spinal fracture or dislocation. Penetrating injuries due to bullets or weapons may also cause primary SCI (Burney et al., Arch Surg 128(5): 596-9 (1993)). More commonly, displaced bone fragments cause penetrating spinal cord or segmental spinal nerve injuries. Extradural pathology may also cause primary SCI. Spinal epidural hematomas or abscesses cause acute cord compression and injury. Spinal cord compression from metastatic disease is a common oncologic emergency. Longitudinal distraction with or without flexion and/or extension of the vertebral column may result in primary SCI without spinal fracture or dislocation. A VLA-1 antagonist can be used to treat a primary spinal injury.

The pathophysiology of secondary SCI involves a multitude of cellular and molecular events that progress over the first few days after injury (Tator, Brain Pathology 5:407-413 (1995)). The most important cause of secondary SCI is vascular injury to the spinal cord caused by arterial disruption, arterial thrombosis, and hypoperfusion due to shock. SCI can be sustained through ischemia from damage or impingement on the spinal arteries. SCI due to ischemia can occur during surgery where aortic blood flow is temporarily stopped. A VLA-1 antagonist described herein can be used to treat or prevent secondary SCI injury.

Spinal cord injury can also be caused by toxicity (Tator, Brain Pathology 5:407-413 (1995)). One of the most compelling toxicity in spinal cord injury is the accumulation and subsequent damage exerted by the excitatory amino acid neurotransmitter. Glutamate induced excitotoxicity causes an elevation of intracellular calcium. Raised intracellular calcium can in turn cause activation of calcium dependent proteases or lipases which cause further damage due to breakdown of cytoskeletal components including neurofilaments and dissolution of cell membranes. The excess production of arachidonic acid and eicosanoids such as prostaglandins may be related to lipid peroxidation and oxygen free radicals. The release of vasoactive eicosanoids from damaged neuronal membranes may in turn cause progressive posttraumatic ischemia by inducing vasospasm. Endogenous opioids may also be involved in the secondary injury process either by their effects on the local or systemic circulation or by direct effects on the injured cord. A VLA-1 antagonist described herein can be used to treat or prevent spinal cord injury resulting from toxicity.

Significant and progressive edema can follow spinal cord injury. It is not known whether the edema is injurious in itself or whether it is an epiphenomenon of another injury mechanism such as ischemia or glutamate toxicity. Edema can spread in the cord from the site of injury for a considerable distance rostrally and caudally in both experimental models and clinical cases.

SCI are classified as complete or incomplete, based on the extent of injury, according to the American Spinal Injury Association (ASIA) Impairment Scale. In complete SCI, there is no sensory and motor function preserved in the lowest sacral segments (Waters et al., Paraplegia 29(9): 573-81 (1991)). In incomplete SCI, sensory or motor function is preserved below the level of injury including the lowest sacral segments (Waters et al., Archives of Physical Medicine and Rehabilitation 75(3): 306-11 (1994)). Incomplete cord lesions may evolve into more complete lesions. More commonly, the injury level rises one or two spinal levels during the hours to days after the initial event.

Other classifications of SCI include central cord syndrome, Brown-Sequard syndrome, anterior cord syndrome, conus medullaris syndrome and cauda equina syndrome. Central cord syndrome is often associated with a cervical region injury leading to greater weakness in the upper limbs than in the lower limbs with sacral sensory sparing. Brown-Sequard syndrome involves a hemisection lesion of the cord, causing a relatively greater ipsilateral proprioceptive and motor loss with contralateral loss of sensitivity to pain and temperature. Anterior cord syndrome is often associated with a lesion causing variable loss of motor function and sensitivity to pain and temperature, while proprioception is preserved. Conus medullaris syndrome is associated with injury to the sacral cord and lumbar nerve roots. This syndrome is characterized by areflexia in the bladder, bowel, and lower limbs, while the sacral segments occasionally may show preserved reflexes (e.g., bulbocavernosus and micturition reflexes). Cauda equina syndrome is due to injury to the lumbosacral nerve roots in the spinal canal, leading to areflexic bladder, bowel, and lower limbs.

Neurogenic shock can result from SCI (Tator, Brain Pathology 5:407-413 (1995)). Neurogenic shock refers to the hemodynamic triad of hypotension, bradycardia, and peripheral vasodilation resulting from autonomic dysfunction and the interruption of sympathetic nervous system control in acute SCI, and is differentiated from spinal and hypovolemic shock. Hypovolemic shock tends to be associated with tachycardia. Spinal shock is defined as the complete loss of all neurologic function, including reflexes and rectal tone, below a specific level that is associated with autonomic dysfunction. An initial increase in blood pressure is noted due to the release of catecholamines, followed by hypotension. Flaccid paralysis, including of the bowel and bladder, is observed, and sometimes sustained priapism develops. These symptoms tend to last several hours to days until the reflex arcs below the level of the injury begin to function again.

Current therapy for SCI aims to improve motor function and sensation in patients with the disorder. Corticosteroids are the mainstay of therapy. Glucocorticoids such as methylprednisolone are thought to reduce the secondary effects of acute SCI, and the use of high-dose methylprednisolone in nonpenetrating acute SCI has become the standard of care in North America.

A VLA-1 antagonist described herein can be used to treat any classification of SCI, or a symptom thereof, as described herein. A VLA-1 antagonist can be used alone or in combination with another known therapy for SCI.

Pharmaceutical Compositions

A VLA-1 antagonist (e.g., an anti-VLA-1 antibody) can be formulated as a pharmaceutical composition, e.g., for administration to a subject to treat stroke, TBI or SCI. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see e.g., Berge, S. M., et al. (1977) J. Pharm. Sci. 66:1-19).

The VLA-1 antagonist can be formulated according to standard methods. Pharmaceutical formulation is a well-established art, and is further described, e.g., in Gennaro (ed.), Remington: The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

In one embodiment, a VLA-1 antagonist (e.g., an anti-VLA-1 antibody) can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intracerebral, intracranial, intracarotid and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the VLA-1 antagonist may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

A VLA-1 antagonist (e.g., an anti-VLA-1 antibody) can be modified, e.g., with a moiety that improves its stabilization and/or retention in circulation, e.g., in blood, serum, or other tissues, e.g., by at least 1.5, 2, 5, 10, or 50 fold. The modified antagonist can be evaluated to assess whether it can reach sites of damage after a stroke, TBI or SCI (e.g., by using a labeled form of the antagonist).

For example, the VLA-1 antagonist (e.g., an anti-VLA-1 antibody) can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, a VLA-1 antagonist can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the VLA-1 antagonist (e.g., an anti-VLA-1 antibody) is used in combination with a second agent, the two agents can be formulated separately or together. For example, the respective pharmaceutical compositions can be mixed, e.g., just prior to administration, and administered together or can be administered separately, e.g., at the same or different times.

Administration

A VLA-1 antagonist described herein (e.g., an anti-VLA-1 antibody) can be administered to a subject, e.g., a human subject, by a variety of methods. For many applications, the route of administration is one of: intravenous injection or infusion (IV), subcutaneous injection (SC), intraperitoneally (IP), or intramuscular injection. In some cases, administration may be directly into the CNS, e.g., intrathecal, intracerebroventricular (ICV), intracerebral or intracranial. The antagonist can be administered as a fixed dose, or in a mg/kg dose.

The dose can also be chosen to reduce or avoid production of antibodies against the antagonist.

The route and/or mode of administration of the blocking agent can also be tailored for the individual case, e.g., by monitoring the subject, e.g., using tomographic imaging, neurological exam, and standard parameters associated with stroke, TBI or SCI, e.g., the assessment criteria described herein.

Dosage regimens are adjusted to provide the desired response, e.g., a therapeutic response or a combinatorial therapeutic effect. Generally, any combination of doses (either separate or co-formulated) of the VLA-1 antagonist (e.g., an anti-VLA-1 antibody) (and optionally a second agent) can be used in order to provide a subject with the agent in bioavailable quantities. For example, doses in the range of 0.025 mg/kg-100 mg/kg, 0.05-50 mg/kg, 0.1-30 mg/kg, 0.1-5 mg/kg, or 0.3-3 mg/kg can be administered.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent.

The VLA-1 antagonist may be administered at least once between about 10 minutes to about 48 hours, more preferably between about 10 minutes and 24 hours, more preferably within 3 hours, after the onset of stroke symptoms or manifestation, TBI symptoms, or SCI symptoms. Single or multiple dosages may be given. Alternatively, or in addition, the antagonist may be administered via continuous infusion. The treatment can continue for days, weeks, months or even years so as to minimize ischemic damage from the stroke, to minimize damage from post-stroke inflammatory events, to prevent another stroke or to minimize damage that might result from a subsequent stroke, to treat primary or secondary TBI or symptoms, or to treat primary or secondary SCI or symptoms.

For example, if a subject is at risk for stroke or has suffered a TIA, the antagonist can be administered before the onset of a stroke as a preventative measure. The duration of such preventative treatment can be a single dosage of the antagonist or the treatment may continue (e.g., multiple dosages), for example, a subject at risk for stroke may be treated with the antagonist for days, weeks, months, or even years so as to prevent a stroke from occurring.

A pharmaceutical composition may include a therapeutically effective amount of an antagonist described herein. Such effective amounts can be determined based on the effect of the administered antagonist, or the combinatorial effect of an antagonist and secondary agent if more than one agent is used. A therapeutically effective amount of an antagonist may also vary according to factors such as the disease state, age, sex, and weight of the individual, and the ability of the compound to elicit a desired response in the individual, e.g., amelioration of at least one disorder parameter, e.g., a stroke, TBI or SCI parameter, or amelioration of at least one symptom of the disorder, e.g., stroke, TBI or SCI. A therapeutically effective amount is also one in which any toxic or detrimental effects of the composition is outweighed by the therapeutically beneficial effects.

Devices and Kits

Pharmaceutical compositions that include a VLA-1 antagonist (e.g., an anti-VLA-1 antibody) can be administered with a medical device. The device can designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include a VLA-1 antagonist, and can be configured to deliver one or more unit doses of the antagonist.

For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

A VLA-1 antagonist (e.g., an anti-VLA-1 antibody) can be provided in a kit. In one embodiment, the kit includes (a) a container that contains a composition that includes a VLA-1 antagonist, and optionally (b) informational material. The informational material can be descriptive, instructional, marketing or other material that relates to the methods described herein and/or the use of the agents for therapeutic benefit. In an embodiment, the kit includes also includes a second agent for treating stroke, TBI or SCI. For example, the kit includes a first container that contains a composition that includes the VLA-1 antagonist, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the VLA-1 antagonist (e.g., an anti-VLA-1 antibody), e.g., in a suitable dose, dosage form, or mode of administration (e.g., a dose, dosage form, or mode of administration described herein), to treat a subject who has had a stroke, TBI or SCI or who is at risk for stroke, TBI or SCI. The information can be provided in a variety of formats, include printed text, computer readable material, video recording, or audio recording, or a information that provides a link or address to substantive material.

In addition to the antagonist, the composition in the kit can include other ingredients, such as a solvent or buffer, a stabilizer, or a preservative. The antagonist can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the VLA-1 antagonist and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

EXAMPLES

Example 1—Effects of Anti-VLA-1 Antibody on Focal Cerebral Ischemia

Protocol

Female C57B6 mice weighing 18-20 g from Charles River Lab were used for this study. Animals were grouped into 2 experimental groups outlined by the following conditions.

| Grouping | Treatment | Dose | Route | N | Surgery |
|---|---|---|---|---|---|
| A | Vehicle (P1.17) | 30 mg/kg | IP | 18 (initial) 12 (final) | MCAO + perfusion |
| B | Anti-VLA-mAB (muHa31/8) | 30 mg/kg | IP | 18 (initial) 12 (final) | MCAO + perfusion |

Following intraperitoneal injection of murine Ha31/8 or P1.17, mice were anaesthetized initially with 2% isofurane and thereafter maintained in 1.0% isofurane in $O_2$, delivered through a face-mask. Rectal temperature was maintained between 36.8 and 37.2° C. using a feedback-regulated heating pad (Harvard Apparatus, Inc. Holliston, Mass.). Regional cerebral blood flow (rCBF) was monitored using a PeriFlux System (Perimed Inc., Sweden) before and during middle cerebral artery occlusion (MCAO), and after reperfusion.

To induce focal cerebral ischemia with reversible occlusion of the middle cerebral artery (MCA), a 7.0 nylon monofilament suture coated with a silicone/hardener mixture (Heraeus Kulzer, Germany) was inserted into the lumen of the right common carotid artery. The suture was advanced 9±1.0 mm from the insertion site through the internal carotid artery until the proximal portion of the anterior cerebral artery, completely occluding the MCA at its origin. Laser Doppler flowmetry measurement of rCBF indicated that the MCA occlusion was successful in both groups because the rCBF dropped to 20% of base line. MCAO lasted two hours; meanwhile, the wound was closed and anesthesia was discontinued. After 2 hours MCA occlusion, the filament was taken out and mice were reperfused for 24 hours. Whether rCBF remained on the previous level was determined. Four animals were excluded from this study because rCBF was found increasing back to more than 50% of previous level 2 hours after MCAO and before reperfusion. All physiologic parameters before, during, and after ischemia were within the normal range and did not differ between groups.

Neurologic deficits were assessed and scored on 30 minutes after MCAO and 24 hours after reperfusion respectively in the open filed. The test was described by Hara et al (1997):

| | | |
|---|---|---|
| 0, | no observable neurologic deficit | (normal), |
| 1, | failure to extent right forepaw | (mild); |
| 2, | circling to the contralateral side | (moderate); |
| 3, | loss of walking or right reflex | (severe). |

The volume of ischemic lesion after MCA occlusion was measured in both groups. The mice were sacrificed by decapitation after 24 hours of reperfusion following 2 hours of MCAO, and brains were rapid removed and sliced into 6 1-mm thick coronal sections using a mouse brain matrix. The brain sections were then stained in 2% 2,3,5-triphenyltetrazolium chloride (TTC, Sigma) at room temperature in the dark for 30 min, then placed in 10% neutral buffered formalin overnight. Brain slices were directly scanned on an image scanner. The lesion was measured on the posterior surface of each section (NIH Image 1.61, US National Institutes of Health). A direct measurement of infarct area in the cortex and striatum was carried out, which was then corrected to eliminate the effect of edema using the following formula:

% indirect infarct area of contralateral cortex=[(contralateral area−ipsilateral nontraumatic area)/contralateral area]×100.

The total infarct volume was calculated by numeric integration of the sequential infarct areas including both the cortex and striatum. Measurements were made after the sections were coded so that the observer was blinded with respect to the previous treatment. Edema was quantified as the % increase in the ischemic hemisphere size compared to the contralateral uninjured hemisphere.

Results

Control antibody-treated mice that underwent MCAO sustained extensive lesions throughout the cortical and subcortical regions of the brain. The ischemic hemisphere was markedly swollen and significant behavioral deficits were observed (e.g., hemiparesis resulting in rotation and limb weakness; see FIG. 1A).

Figure 1B:
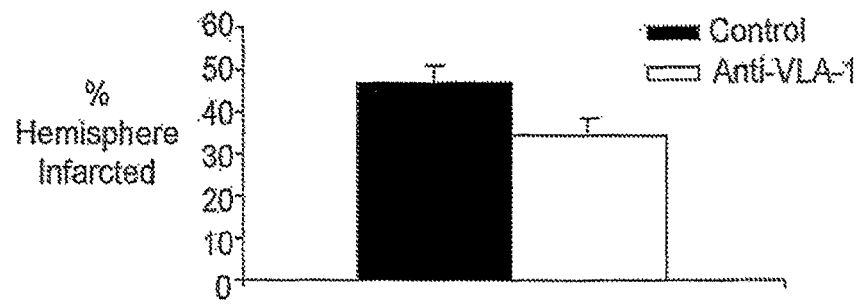
FIG. 1B is a graph of the percentage of hemisphere infarcted in control- and anti-VLA-1 antibody-treated mice following MCAO.
Figure 1C:
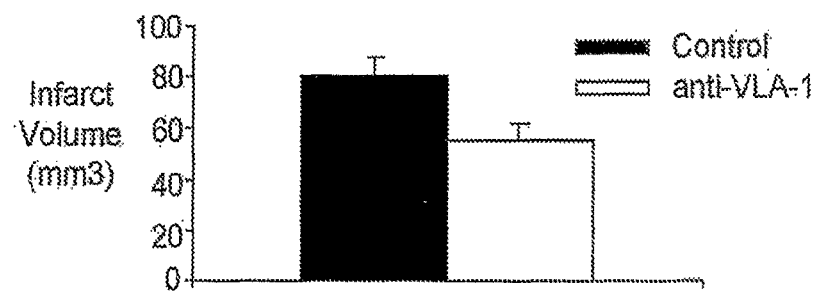
FIG. 1C is a graph of infarct volume in control- and anti-VLA-1 antibody-treated mice following MCAO.
Figure 1D:
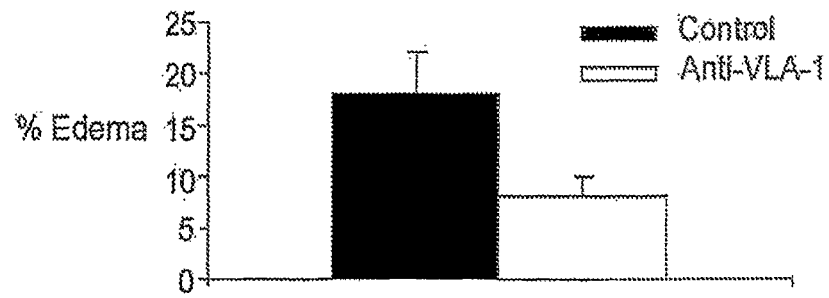
FIG. 1D is a graph of percent edema in control- and anti-VLA-1 antibody-treated mice following MCAO.
Figure 2A:
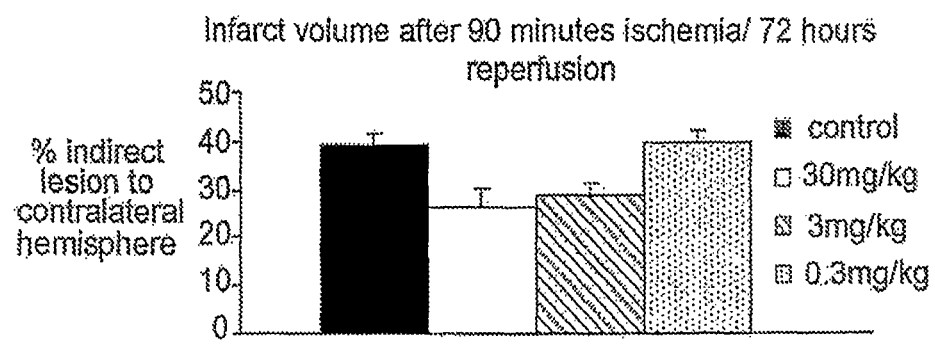
FIG. 2A is a graph of infarct volume in control- and anti-VLA-1 antibody-treated mice following MCAO.
Figure 2B:
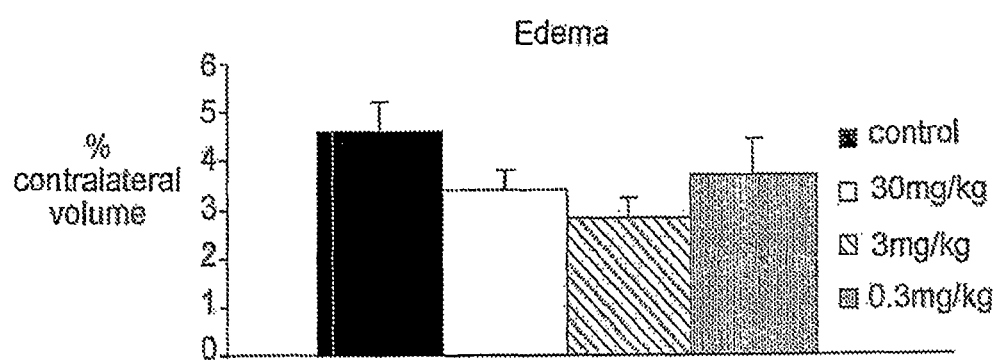
FIG. 2B is a graph of percent edema in control- and anti-VLA-1 antibody-treated mice following MCAO.

Mice treated with control antibody (P1.17) sustained infarcts spanning 47.1±3.8% of the ischemic hemisphere. Mice treated with anti-VLA-1 antibody sustained significantly smaller infarcts spanning only 34.3±4.2% of the ischemic hemisphere (P<0.02, unpaired Students' T-test, n=12 per group) representing a 24% reduction in infarct size (FIG. 1B). In absolute volumetric terms, this was equivalent to a mean control infarct volume of 80.8±6.8 $mm^3$ vs. a mean anti-VLA-1 treated infarct volume of 55.63±6.3 $mm^3$ (FIG. 1C). Brain swelling or edema was calculated as the percentage increase in hemisphere size of the infarcted hemisphere compared to the undamaged contra-lateral hemisphere. Control (P1.17)-treated mice sustained a mean increase in hemisphere size of 18.1±% compared to anti-VLA-1 (Ha/31/8)-treated mice that sustained an increase in hemisphere size of 8.2%±1.9% (P<0.05, Unpaired Students' T-test n=12 per group. FIG. 1D). FIG. 2 demonstrates a dose response using three concentrations of the anti-VLA-1 (Ha31/8) antibody, and shows that 3 mg/kg of the antibody was as effective as 30 mg/kg in reducing both infarct volume (FIG. 2A) and edema (FIG. 2B).

These data demonstrate the neuroprotective and anti-inflammatory effect of inhibition of VLA-1 in a model of reversible middle cerebral artery occlusion in the mouse. The pathology of this model is clinically representative of the human condition of stroke and other CNS ischemic injuries such as TBI and SCI, and the present data suggest that inhibitors of VLA-1 may be of significant benefit in the treatment of these and other ischemia related disorders.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a traumatic brain injury (TBI) in a subject, the method comprising administering to the subject a humanized AQC2 anti-VLA-1 (Very Late Activation Antigen-I) antibody, or an antigen-binding fragment thereof, wherein the anti-VLA-1 antibody, or antigen-binding fragment thereof, is first administered within 48 hours of the TBI, and wherein the anti-VLA-1 antibody, or antigen-binding fragment thereof, reduces infarct size in a hemisphere affected by the TBI, such that the percentage of the hemisphere infarcted is 40% or less, and wherein the anti-VLA-1 antibody or antigen-binding fragment thereof is administered at a dosage from 0.1 mg/kg per day to 5 mg/kg per day.

2. The method of claim 1, wherein the TBI is a contusion, bruise, laceration or hematoma.

3. The method of claim 1, wherein the administering step reduces the infarct size by at least 10% in the hemisphere affected by the TBI, as compared to an infarct size in an untreated subject.

4. The method of claim 1, wherein the administering step reduces the infarct size by at least 20% in the hemisphere affected by the TBI, as compared to an infarct size in an untreated subject.

5. The method of claim 1, wherein the administering step reduces edema, such that the size of the hemisphere affected by the TBI is increased by no more than 10% following the TBI.

6. A method of treating a stroke in a subject, the method comprising administering to the subject a humanized AQC2 anti-VLA-1 (Very Late Activation Antigen-1) antibody, or an antigen-binding fragment thereof, wherein the anti-VLA-1 antibody, or antigen-binding fragment thereof, is first administered within 48 hours of the stroke, and wherein the anti-VLA-1 antibody, or antigen-binding fragment thereof, reduces infarct size in a hemisphere affected by the stroke, such that the percentage of the hemisphere infarcted is 40% or less, and wherein the anti-VLA-1 antibody or antigen-binding fragment thereof is administered at a dosage from 0.1 mg/kg per day to 5 mg/kg per day.

7. The method of claim 6, wherein the humanized AQC2 anti-VLA-1 antibody, or antigen-binding fragment thereof, is produced by a hybridoma having ATCC Deposit No. PTA3275.

8. The method of claim 6, wherein the anti-VLA-1 antibody or antigen-binding fragment thereof is effective to improve neurologic function.

9. The method of claim 6, wherein the stroke is an ischemic stroke.

10. The method of claim 6, wherein the stroke is an hemorrhagic stroke.

11. The method of claim 6, wherein the subject is a mammal.

12. The method of claim 11, wherein the subject is a human.

13. The method of claim 6, wherein the anti-VLA-1 antibody or antigen-binding fragment thereof is administered intravenously or parenterally.

14. The method of claim 6, wherein the anti-VLA-1 antibody or antigen-binding fragment thereof is administered at least twice within 7 days after the stroke.

15. The method of claim 6, wherein the administering step reduces the infarct size by at least 10% in the hemisphere affected by the stroke, as compared to an infarct size in an untreated subject.

16. The method of claim 6, wherein the administering step reduces the infarct size by at least 20% in the hemisphere affected by the stroke, as compared to an infarct size in an untreated subject.

17. The method of claim 6, wherein the administering step reduces edema, such that the size of the hemisphere affected by the stroke is increased by no more than 10% following the stroke.

18. The method of claim 6, wherein the anti-VLA-1 antibody or antigen-binding fragment thereof is administered in combination with another therapeutic agent.

19. The method of claim 18, wherein the other therapeutic agent is selected from the group consisting of an antiplatelet agent, a thrombolytic enzyme, an aggregation inhibitor, a glycoprotein IIb/IIIa inhibitor, a glycosaminoglycan, a thrombin inhibitor, an anticoagulant, heparin, coumarin, tPA, GCSF, streptokinase, urokinase, Ancrod, acetylsalicylic acid, melatonin, and a caspase inhibitor.

\* \* \* \* \*